United States Patent
Barnes et al.

(10) Patent No.: US 9,750,508 B1
(45) Date of Patent: Sep. 5, 2017

(54) INSULATED PEDICLE ACCESS SYSTEM AND RELATED METHODS

(75) Inventors: Jeff Barnes, San Diego, CA (US); Eric Finley, Poway, CA (US); Thomas Scholl, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 1217 days.

(21) Appl. No.: 12/945,705

(22) Filed: Nov. 12, 2010

Related U.S. Application Data

(60) Provisional application No. 61/260,326, filed on Nov. 11, 2009, provisional application No. 61/299,866, filed on Jan. 29, 2010.

(51) Int. Cl.
*A61B 17/16* (2006.01)

(52) U.S. Cl.
CPC .................. *A61B 17/1671* (2013.01)

(58) Field of Classification Search
CPC ............ A61B 17/7092; A61B 17/1671; A61B 5/150633
USPC .... 606/86 R, 96, 102–104, 86 A, 32, 41, 43, 606/44, 185; 604/164.01; 607/115, 117
See application file for complete search history.

(56) References Cited

U.S. PATENT DOCUMENTS

| | | |
|---|---|---|
| 3,540,447 A | 11/1970 | Howe |
| 3,595,230 A | 7/1971 | Suyeoka |
| 3,598,108 A | 8/1971 | Jamshidi |
| 3,850,158 A | 11/1974 | Elias |
| 4,230,123 A | 10/1980 | Hawkins |
| 4,256,119 A | 3/1981 | Gauthier |
| 4,262,676 A | 4/1981 | Jamshidi |
| 4,266,555 A | 5/1981 | Jamshidi |
| 4,314,565 A | 2/1982 | Lee |
| 4,356,828 A | 11/1982 | Jamshidi |
| 4,592,369 A | 6/1986 | Davis |
| 4,609,370 A | 9/1986 | Morrison |
| 4,630,616 A | 12/1986 | Tretinyak |
| 4,702,738 A | 10/1987 | Spencer |
| 4,759,377 A | 7/1988 | Dykstra |
| 4,775,369 A | 10/1988 | Schwartz |
| 4,793,363 A | 12/1988 | Ausherman |
| 4,838,282 A | 6/1989 | Strasser |
| 4,964,411 A | 10/1990 | Johnson |
| 5,147,327 A | 9/1992 | Johnson |
| 5,151,089 A | 9/1992 | Kirk |

(Continued)

FOREIGN PATENT DOCUMENTS

| | | |
|---|---|---|
| EP | 0607688 A1 | 7/1994 |
| EP | 0754431 A1 | 1/1997 |

(Continued)

OTHER PUBLICATIONS

Anderson, D.G. et al., "Pedicle screws with high electrical resistance: a potential source of error with stimulus-evoked EMG", Spine, 27(14), (Jul. 15, 2002), 1577-1581.

(Continued)

*Primary Examiner* — David Bates
(74) *Attorney, Agent, or Firm* — Stephen H. Hall; Bradley Arant Boult Cummings LLP

(57) ABSTRACT

The present invention relates to devices and methods directed towards accessing and forming holes in bone tissue including penetrating vertebral bones during surgical treatments of the spine, for example, to cannulate pedicles and form pilot holes for placing pedicle screws.

23 Claims, 35 Drawing Sheets

(56) References Cited

U.S. PATENT DOCUMENTS

| | | |
|---|---|---|
| 5,196,015 A | 3/1993 | Neubardt |
| 5,201,721 A | 4/1993 | Lee |
| 5,242,418 A | 9/1993 | Weinstein |
| 5,279,584 A | 1/1994 | Dillard |
| 5,357,974 A | 10/1994 | Baldridge |
| 5,368,046 A | 11/1994 | Scarfone |
| 5,415,645 A | 5/1995 | Friend |
| 5,474,558 A | 12/1995 | Neubardt |
| 5,480,440 A | 1/1996 | Kambin |
| 5,549,656 A | 8/1996 | Reiss |
| 5,645,076 A | 7/1997 | Yoon |
| 5,758,655 A | 6/1998 | Como Rodriguez |
| 5,807,275 A | 9/1998 | Jamshidi |
| 5,928,162 A | 7/1999 | Giurtino |
| 5,928,163 A | 7/1999 | Roberts |
| 5,928,243 A * | 7/1999 | Guyer ............... A61B 17/1671 606/102 |
| 6,033,369 A | 3/2000 | Goldenberg |
| 6,038,477 A | 3/2000 | Kayyali |
| 6,063,037 A | 5/2000 | Mittermeier |
| 6,104,960 A | 8/2000 | Duysens |
| 6,110,128 A | 8/2000 | Andelin |
| 6,181,961 B1 | 1/2001 | Prass |
| 6,221,029 B1 | 4/2001 | Mathis |
| 6,261,241 B1 | 7/2001 | Burbank |
| 6,302,852 B1 | 10/2001 | Fleming |
| 6,306,100 B1 | 10/2001 | Prass |
| 6,312,394 B1 | 11/2001 | Fleming |
| 6,340,351 B1 | 1/2002 | Goldenberg |
| 6,468,279 B1 | 10/2002 | Reo |
| 6,471,709 B1 * | 10/2002 | Fawzi et al. ............... 606/114 |
| 6,475,190 B2 | 11/2002 | Young |
| 6,554,778 B1 | 4/2003 | Fleming |
| 6,558,353 B2 | 5/2003 | Zohmann |
| 6,575,919 B1 | 6/2003 | Reiley |
| 6,579,244 B2 | 6/2003 | Goodwin |
| 6,623,437 B2 | 9/2003 | Hinchliffe |
| 6,719,692 B2 | 4/2004 | Kleffner |
| D489,456 S | 5/2004 | Groenke |
| 6,796,985 B2 | 9/2004 | Bolger |
| 6,819,956 B2 | 11/2004 | DiLorenzo |
| 6,849,047 B2 | 2/2005 | Goodwin |
| 6,855,105 B2 | 2/2005 | Jackson |
| 6,875,183 B2 | 4/2005 | Cervi |
| 6,929,606 B2 | 8/2005 | Ritland |
| 7,018,343 B2 | 3/2006 | Plishka |
| 7,025,768 B2 * | 4/2006 | Elliott ............... 606/45 |
| 7,063,703 B2 | 6/2006 | Reo |
| 7,081,122 B1 | 7/2006 | Reiley |
| 7,081,123 B2 * | 7/2006 | Merboth et al. ............... 606/185 |
| 7,089,059 B1 | 8/2006 | Pless |
| 7,160,306 B2 * | 1/2007 | Matsuzaki et al. ......... 606/86 R |
| 7,278,972 B2 * | 10/2007 | Lamoureux et al. ......... 600/567 |
| 7,338,456 B2 * | 3/2008 | Goldenberg ............... 600/564 |
| 7,384,400 B2 * | 6/2008 | Goldenberg ............... 600/564 |
| 7,399,306 B2 | 7/2008 | Reiley |
| 7,468,041 B2 | 12/2008 | Rhodes |
| 7,468,042 B2 | 12/2008 | Turovskiy |
| 7,470,236 B1 | 12/2008 | Kelleher |
| 7,942,826 B1 * | 5/2011 | Scholl ............... A61B 5/0492 600/554 |
| 8,005,535 B2 * | 8/2011 | Gharib et al. ............... 600/546 |
| 2001/0029387 A1 | 10/2001 | Wolf |
| 2002/0072688 A1 | 6/2002 | Burbank |
| 2003/0191414 A1 | 10/2003 | Reiley |
| 2004/0225228 A1 | 11/2004 | Ferree |
| 2005/0033380 A1 | 2/2005 | Tanner |
| 2005/0192575 A1 | 9/2005 | Pacheco |
| 2005/0203441 A1 | 9/2005 | Voegele |
| 2006/0025703 A1 | 2/2006 | Miles |
| 2006/0173521 A1 * | 8/2006 | Pond et al. ............... 607/116 |
| 2006/0178666 A1 * | 8/2006 | Cosman et al. ............... 606/41 |
| 2007/0083167 A1 | 4/2007 | Smith |
| 2007/0197935 A1 | 8/2007 | Reiley |
| 2007/0260184 A1 | 11/2007 | Justis |
| 2007/0260255 A1 | 11/2007 | Haddock |
| 2008/0071302 A1 | 3/2008 | Castillo |
| 2008/0228104 A1 | 9/2008 | Uber |
| 2009/0194446 A1 | 8/2009 | Miller |
| 2009/0264940 A1 * | 10/2009 | Beale et al. ............... 606/86 R |

FOREIGN PATENT DOCUMENTS

| | | |
|---|---|---|
| WO | WO-9956631 | 11/1999 |
| WO | WO-0137728 | 5/2001 |
| WO | WO-03037170 | 12/2004 |
| WO | WO-2005013805 | 2/2005 |

OTHER PUBLICATIONS

Bose, Bikash et al., "Neurophysiologic Monitoring of Spinal Nerve Root Function During Instrumented Posterior Lumbar Spine Surgery", Spine, 27(13), (2002), 1444-1450.

"Brackman II EMG System", Medical Electronics, (1994), 4 pgs.

Calancie, Blair, "Stimulus-Evoked EMG Monitoring During Transpedicular Lumbosacral Spine Instrumentation", Spine, 19(24), (1994), 2780-2786.

Clements, David, "Evoked and Spontaneous Electromyography to Evaluate Lumbosacral Pedicle Screw Placement", Spine, 19(24), (1996), 600-604.

Danesh-Clough T., "The use of evoked EMG in detecting misplaced thoracolumbar pedicle screws", Spine, 26(12), (Jul. 15, 2001), 1313-1316.

Darden, B. V., "A comparison of impedance and electromyogram measurements in detecting the presence of pedicle wall breakthrough", Spine, 23(2), (Jan. 15, 1998), 256-262.

Ebraheim, N. A., "Anatomic relations between the lumbar pedicle and the adjacent neural structures", Spine, 22(20), (Oct. 15, 1997), 2338-2341.

Glassman, Steven, "A Prospective Analysis of Intraoperative Electromyographic Monitoring of Pedicle Screw placement With Computed Tomographic Scan Confirmation", Spine, 20(12), (1995), 1375-1379.

Holland, Neil, "Intraoperative Electromyography During Thoracolumbar Spinal Surgery", Spine, 23(17), (1998), 1915-1922.

Holland, N. R., "Higher electrical stimulus intensities are required to activate chronically compressed nerve roots. Implications for intraoperative electromyographic pedicle screw testing", Spine, 23(2), (Jan. 15, 1998), 224-227.

Journee, H. L "System for Intra-Operative Monitoring of the Cortical Integrity of the Pedicle During Screw Placement in Low-Back Surgery: Design and Clinical Results", Sensory and neuromuscular diagnostic instrumentation and data analysis, 18th Annual international Conference on Engineering in Medicine and Biology Society, 1(31), (Oct. 1996), 144-145.

Lenke, Lawrence, "Triggered Electromyographic Threshold for Accuracy of Pedicle Screw Placement", Spine, 20(14), (1995), 1585-1591.

Maguire, J., "Evaluation of Intrapedicular Screw Position Using Intraoperative Evoked Electromyography", Spine, 20(14), (1995), 1068-1074.

Minahan, R. E., "The effect of neuromuscular blockade on pedicle screw stimulation thresholds", Spine, 20(9), (Oct. 1, 2000), 2526-2530.

"Neurovision SE Nerve Locator/Monitor", RLN Systems Inc. Operators Manual , (1999), 22 pgs.

"NIM-Spine System Neural Integrity Monitor", Medtronic Sofamor Danek USA, (2004), 2 pgs.

"The Brackman II EMG Monitoring System", Medical Electronics Co. Operator's Manual Version 1.1, (1995), 50 pgs.

"The Nicolet Viking IV", Nicolet Biomedical Products , (1999), 6 pgs.

Tolekis, J, "The Usefulness of Electrical Stimulation for Assessing Pedicle Screw Replacements", Journal of Spinal Disorder, 13(4), (2000), 283-289.

(56) References Cited

OTHER PUBLICATIONS

Welch, "Evaluation with evoked and spontaneous electromyography during lumbar instrumentation: a prospective study", J. Neurosurg, 87 , (Sep. 1997), 397-402.

* cited by examiner

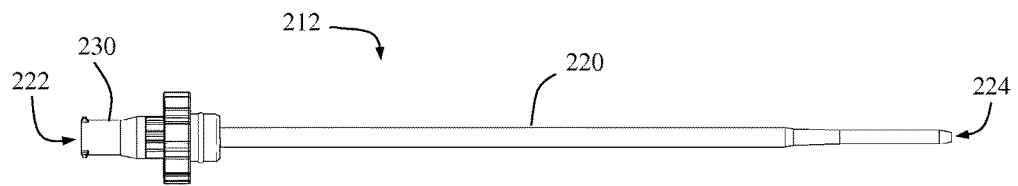
FIG. 35
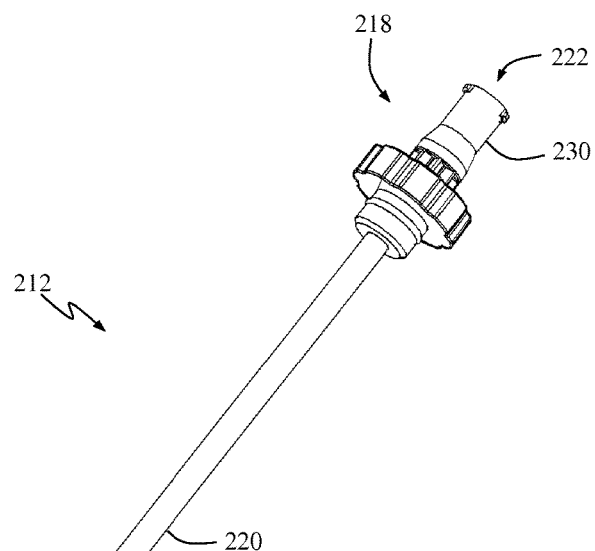
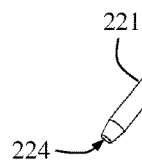
FIG. 36

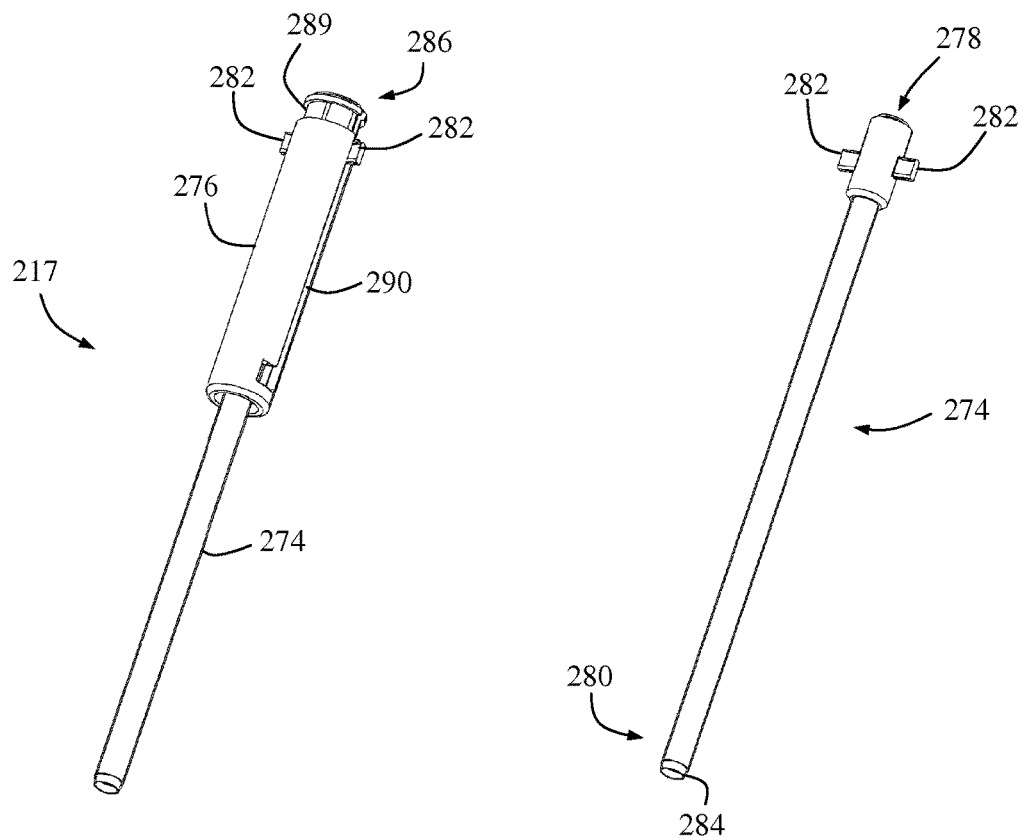
FIG. 46  FIG. 47
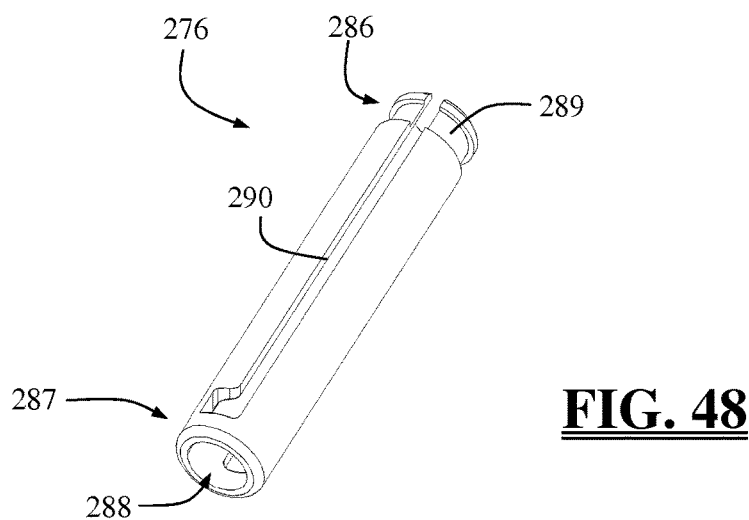
FIG. 48

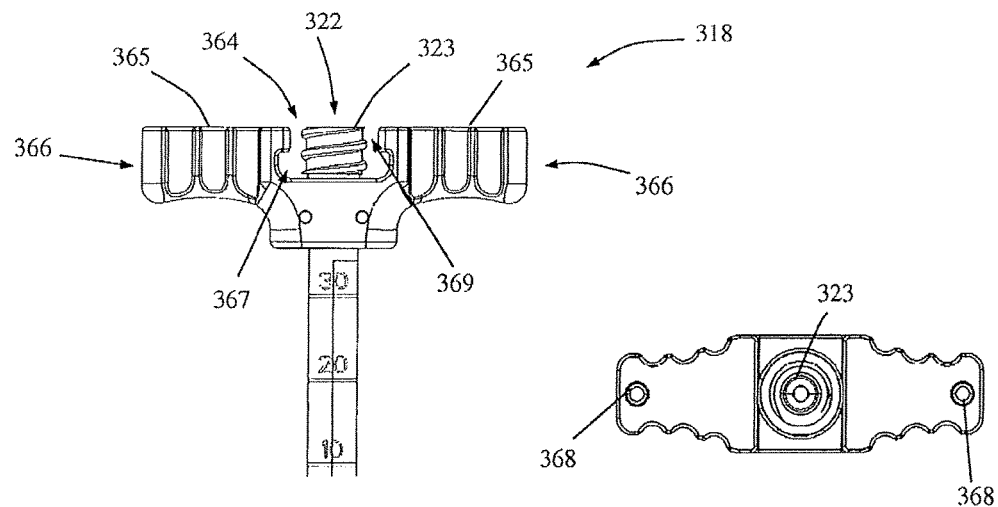
FIG. 58
FIG. 59
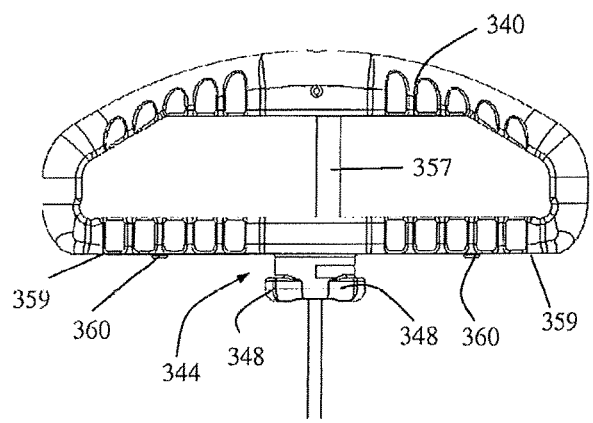
FIG. 60
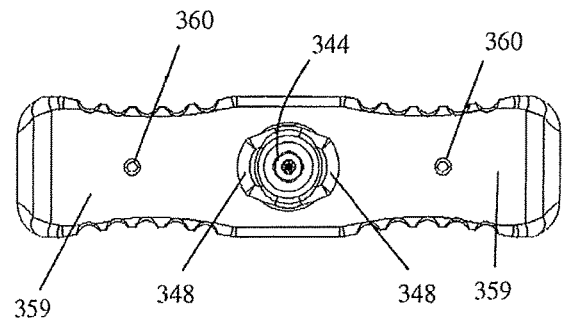
FIG. 61

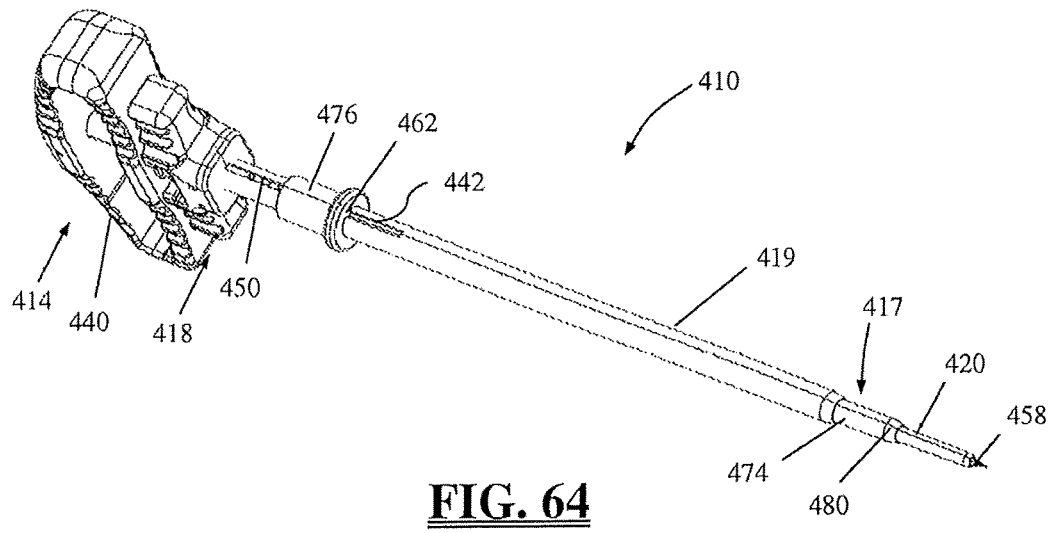
FIG. 64
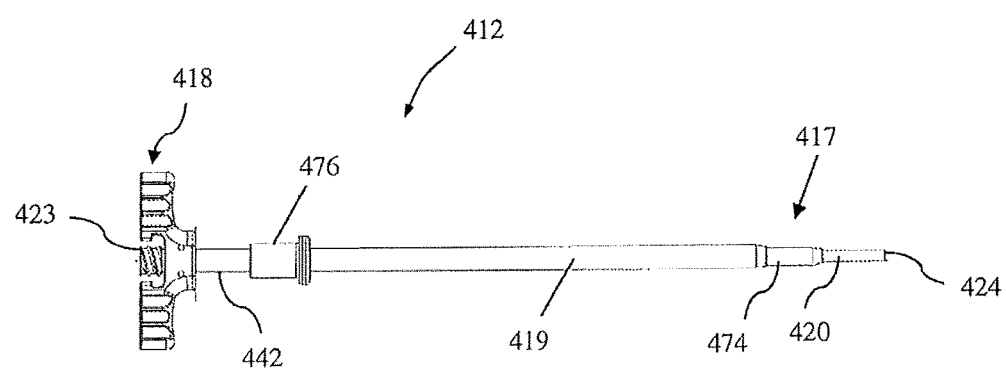
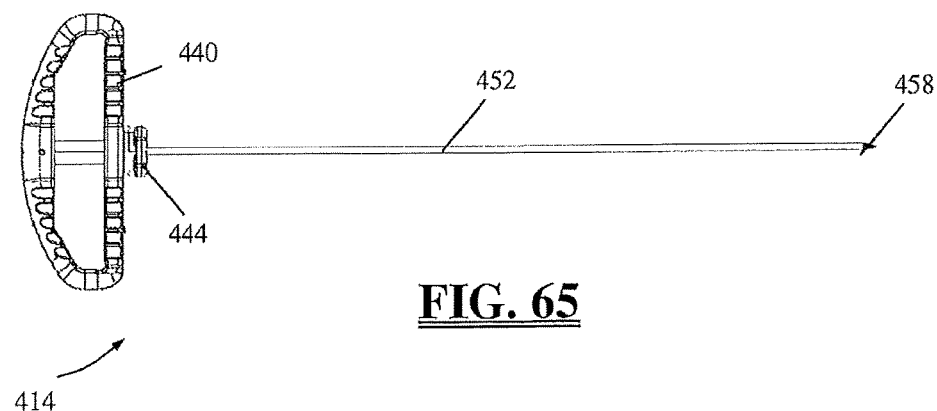
FIG. 65

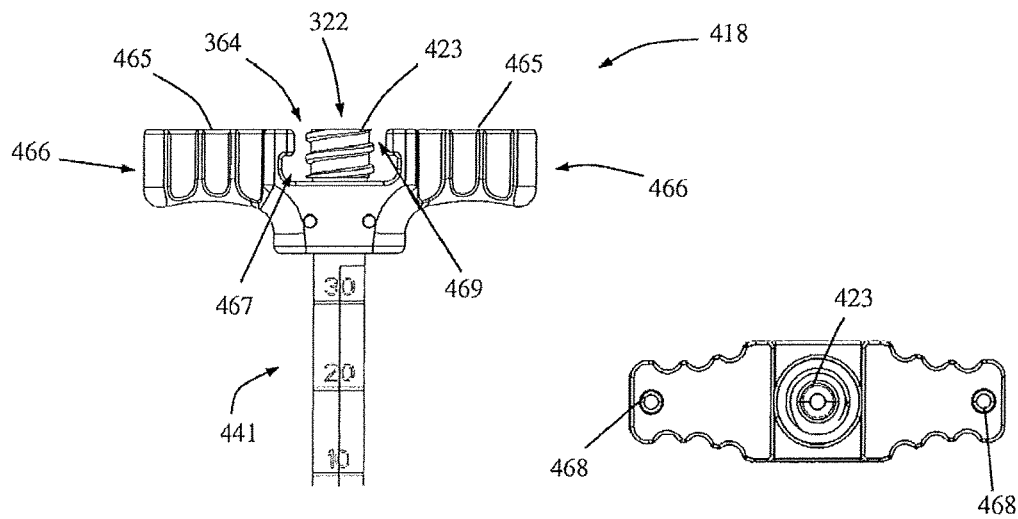
FIG. 69
FIG. 70
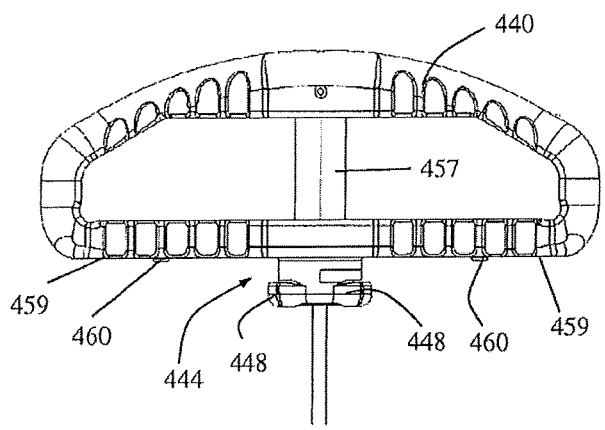
FIG. 71
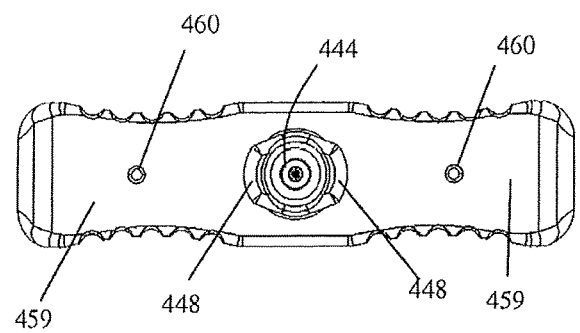
FIG. 72

INSULATED PEDICLE ACCESS SYSTEM AND RELATED METHODS

CROSS-REFERENCE TO RELATED APPLICATIONS

This Application claims the benefit of priority from U.S. Provisional Patent Application Ser. No. 61/260,326, filed on Nov. 11, 2009, and U.S. Provisional Patent Application Ser. No. 61/299,866, filed on Jan. 29, 2010, the entire contents of which are each incorporated by reference into this disclosure as if set forth in their entireties herein.

FIELD

The present invention relates to devices and methods directed towards accessing and forming holes in bone tissue including penetrating vertebral bones during surgical treatments of the spine, for example, to cannulate pedicles and form pilot holes for placing pedicle screws.

BACKGROUND

An emerging trend in spinal surgery is to perform surgery in a minimally invasive or minimal access fashion to avoid the trauma of so-called open or "direct access" procedures. A specific area of interest is in the placement of pedicle screws, which are typically employed to effect posterior fixation in spinal fusion procedures. While great strides are being made in this area, a risk exists (as it does in open procedures) that the pedicle may become breached, cracked, or otherwise compromised during the procedure. If the pedicle (or more specifically, the cortex of the medial wall, lateral wall, superior wall and/or inferior wall) is breached, cracked, or otherwise compromised, the patient may experience pain or neurologic deficit due to unwanted contact between the pedicle screw and exiting nerve roots. This often necessitates revision surgery, which can be painful and costly, both in terms of recovery time and hospitalization.

Some attempts to minimize the risk of a pedicle breach involve capitalizing on the insulating characteristics of bone and the conductivity of the exiting nerve roots themselves to perform pedicle integrity assessments. That is, if the wall of the pedicle is breached, a stimulation signal applied to the pedicle screw and/or the pilot hole (prior to screw introduction) will cause the various muscle groups coupled to the exiting nerve roots to contract. If the pedicle wall has not been breached, the insulating nature of the pedicle will prevent the stimulation signal from innervating the given nerve roots such that the associated muscle groups will not twitch. Traditional EMG monitoring systems may be employed to augment the ability to detect such innervation.

One period during a pedicle screw procedure in which the risk of a pedicle breach is prevalent is during the initial access of the pedicle. Typically, initial access to a pedicle may be achieved by inserting a needle to the target site and driving the needle point into the pedicle, creating a pilot hole. Due to the size and shape of the typical needle, however, manipulation and maneuvering of the needle may be awkward or difficult, increasing the risk of complication. Additionally, the pedicle may be breached and nerve damage done during the initial drive of the needle into the pedicle, before a pedicle integrity test assessment may be performed.

A problem that may arise when various medical instruments are electrified and used with traditional EMG monitoring systems is that different instruments may produce different EMG stimulation thresholds. For example, an electrified needle may exhibit a threshold stimulation of approximately 5-6 mA, while a bone screw placed in the same location may exhibit a threshold stimulation of approximately 16-20 mA. This can be problematic in that an electrified needle may tend to indicate a breach in the pedicle wall when in fact the pedicle wall is intact.

The present invention is directed at eliminating, or at least improving upon, the shortcomings of the prior art.

SUMMARY

This application describes devices and methods for accessing and forming holes in tissue. The tissue may be bone tissue, and particularly spinal bones including vertebral pedicles. The devices can penetrate the vertebral bones during surgical treatments of the spine. Electrical stimulation signals may be deliverable to the tissue through the devices. The electrical stimulation signals may be used to monitor the integrity of the tissue as the devices are advanced into the tissue.

According to one example, a needle assembly system for use in a medical procedure is described. The needle assembly includes a cannula assembly having concentric inner and outer cannulas. The inner cannula has a distal end and a first length. The outer cannula has a distal end and a second length shorter than the first length. The cannula assembly also includes an insulated sheath situated between the inner cannula and the outer cannula. The insulated sheath is movable between a position in which a distal end of the insulated sheath is proximate the distal end of the inner cannula and a position in which a distal end of the insulated sheath is proximate the distal end of the outer cannula. The needle assembly also includes a stylet disposed through the inner cannula and having a shaped tip that protrudes from the distal end of the inner cannula.

According to another aspect of the system the insulated sheath is biased towards the position proximate the distal end of the inner cannula. A spring situated above the insulated sheath and between the inner cannula and the outer cannula that biases the insulated sheath towards the distal end of the inner cannula.

According to another aspect of the system the outer cannula is also insulated.

According to another aspect of the system a connector situated outside the outer cannula is attached to the insulated sheath. The connector may attach to the insulted sheath through at least one elongated slot proximate a distal end of the outer cannula. The outer cannula may also include graduated depth markers and the position of the connector relative to the depth marker provides an indication of penetration depth into tissue.

According to another aspect of the system the needle assembly also includes a handle. The handle may include an upper portion and a lower portion separable from the upper portion. The upper portion may be connected to the stylet and the lower portion may be connected to the cannula assembly. The upper portion and lower portion may be lockable to one another to lock the cannula assembly and the stylet together.

According to another aspect of the system the needle assembly includes a contact that receives electrical stimulation signals from a stimulator. The contact may be a conductive surface situated within the upper handle portion attached to the sylet. The contact may be configured to engage a stimulation clip associated with the stimulator. The upper portion of the handle may include a cutout region that securely engages the stimulation clip.

According to another aspect of the system the sylet is removable from the cannula assembly. A k-wire may also be included that is advanceable through the inner cannula after the sylet has been removed.

According to another aspect of the system the shaped tip and distal end of the inner cannula are adapted to form a hole in bone and a distal end of the insulated sheath is adapted to engage a surface of the bone when the shaped tip and distal end of the inner cannula are advanced into bone such that the insulated sheath slides relative to the inner cannula and outer cannula as said the shaped tip and distal end of the inner cannula are advanced deeper into the bone exposing the exterior of inner cannula to the interior of the bony.

According to another example, there is described a surgical needle assembly. The surgical needle assembly includes a cannula assembly having concentric inner and outer cannulas. The inner cannula has a distal end and a first length. The outer cannula has a distal end and a second length shorter than the first length. The cannula assembly also has a handle portion. The needle assembly also an insulated sheath situated between the inner cannula and the outer cannula. The insulated sheath is spring biased to a first position in which a distal end of the insulated sheath is proximate the distal end of the inner cannula. The insulated sheath is also movable between the first position and a second position in which a distal end of the insulated sheath is proximate the distal end of the outer cannula, and a handle portion. The needle assembly also includes a stylet removably disposed through the inner cannula and having a shaped tip adapted to penetrate bone that protrudes from the distal end of the inner cannula. The stylet also includes a handle portion lockingly mateable with the handle portion of the cannula assembly.

According to another aspect, the needle assembly include a connector situated outside the outer cannula is attached to the insulated sheath. The outer cannula may include graduated depth markers and the position of the connector relative to the depth marker may provide an indication of penetration depth into the bone.

According to another aspect, the needle assembly includes a contact that receives electrical stimulation signals from a stimulator. The contact may be a conductive surface situated within the upper handle portion attached to the sylet. The contact is configured to engage a stimulation clip associated with the stimulator.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIGS. 35-36 are side and perspective views, respectively, of a cannula forming part of the pedicle access system of FIG. 31;

FIG. 46 is a perspective view of a retractable insulation sheath forming part of the pedicle access system of FIG. 31;

FIG. 47 is a perspective view of an insulation tube forming part of the retractable insulation sheath of FIG. 46;

FIG. 48 is a perspective view of a retraction tube forming part of the retractable insulation sheath of FIG. 46;

FIGS. 58-59 are enlarged front and bottom pictures of the proximal end of the cannula of FIG. 56;

FIGS. 60-61 are enlarged front and bottom pictures of the proximal end of the stylet of FIG. 57;

FIG. 64. is a perspective view of a pedicle access system of another embodiment of the present invention;

FIG. 65 a partially exploded view of the pedicle access system of FIG. 64;

FIGS. 69-70 are enlarged front and bottom pictures of the proximal end of the cannula of FIG. 65;

FIGS. 71-72 are enlarged front and bottom pictures of the proximal end of the stylet of FIG. 65.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The insulated pedicle access system and related methods disclosed herein boast a variety of inventive features and components that warrant patent protection, both individually and in combination.

Figure 1:
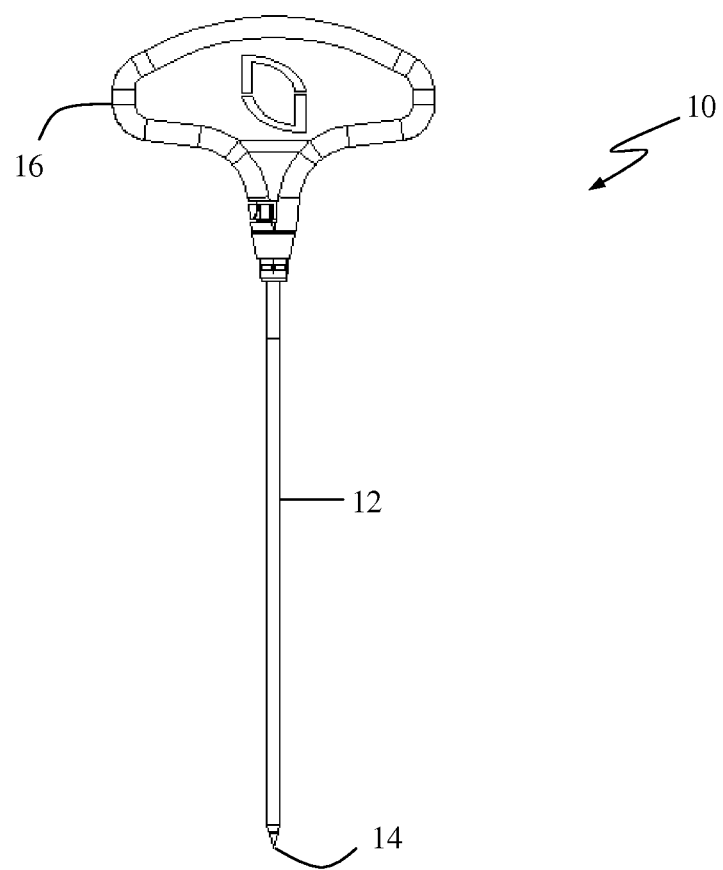
FIG. 1 is a plan view of an example of a pedicle access system according to one embodiment of the present invention.

FIG. 1 illustrates an example of a pedicle access system 10 according to one embodiment of the present invention. The pedicle access system 10 includes a cannula 12, a stylet 14, and a T-handle 16. As will be described with greater detail below, the pedicle access system 10 may be used to percutaneously approach the pedicle, initiate pilot hole formation, and conduct a stimulation signal to the target site for the purposes of performing a pedicle integrity assessment during formation of the pilot hole. To do this, the cannula 12 and stylet 14 may be lockingly mated to form a cannula/stylet combination 15 which may be inserted through an operating corridor to the pedicle target site, using the T-handle 16 to facilitate easy movement and positioning of the cannula/stylet combination 15. The cannula/stylet combination 15 may be driven into the bone at the target site to form a pilot hole while a stimulation signal is applied to the pedicle access system 10 and conducted to the target site to assess the integrity of the pedicle during hole formation. The T-handle 16 may be detached from the cannula/stylet combination 15 to facilitate the use of various surgical tools (such as by way of example only a forceps, mallet, or needle driver) after proper positioning of the cannula 12 and stylet 14. Additionally, removal of the T-handle after proper positioning of the cannula/stylet combination 15 provides a less obstructed view of the operating corridor and surgical target site. As shown and described herein, the cannula 12 and stylet 14 are generally cylindrical in shape. However, it should be understood that cannula 12 and stylet 14 may be provided in any suitable shape having any suitable cross-section (e.g. generally oval or polygonal) without deviating from the scope of the present invention.

Figure 2:
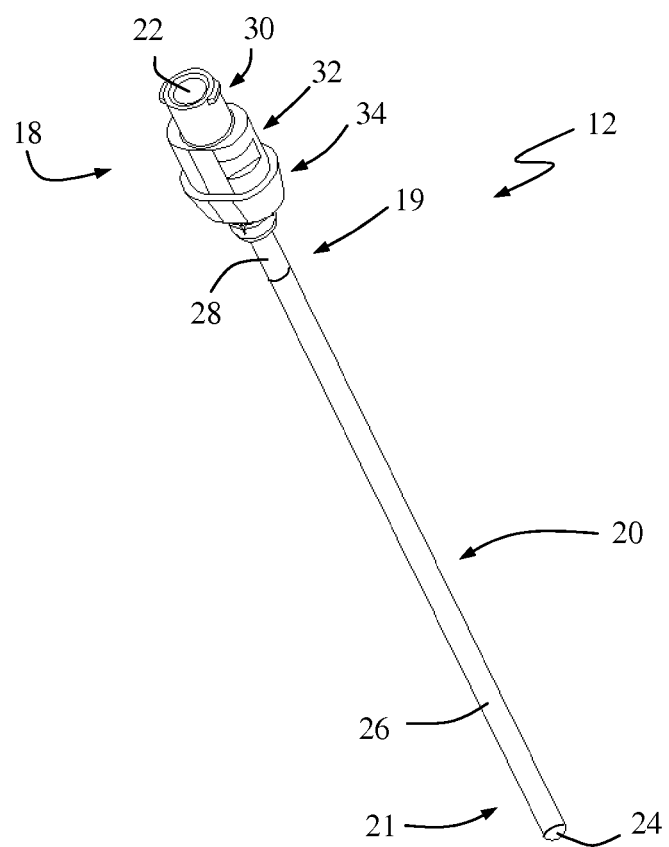
FIG. 2 is a perspective view of a cannula forming part of the pedicle access system of FIG. 1.

FIG. 2 illustrates an example of a cannula 12 forming part of pedicle access system 10. Cannula 12 includes a coupling element 18 and an elongated shaft 20. An interior lumen extends through the cannula 12 from a first opening 22 located at a proximal region 30 of the coupling element 18 to a second opening 24 located at a distal end 21 of the elongated shaft 20. Elongated shaft 20 may be composed of any conductive material such as metal, for example. A polymeric coating is provided on a substantial portion of the exterior surface of elongated shaft 20 such that elongated shaft 20 comprises an insulated portion 26 and an uninsulated portion 28. Although elongated shaft 20 is shown having a single uniform diameter, it will be appreciated that one or more diameter changes may be incorporated along the elongated shaft 20 without deviating from the scope of the present invention.

Figure 3:
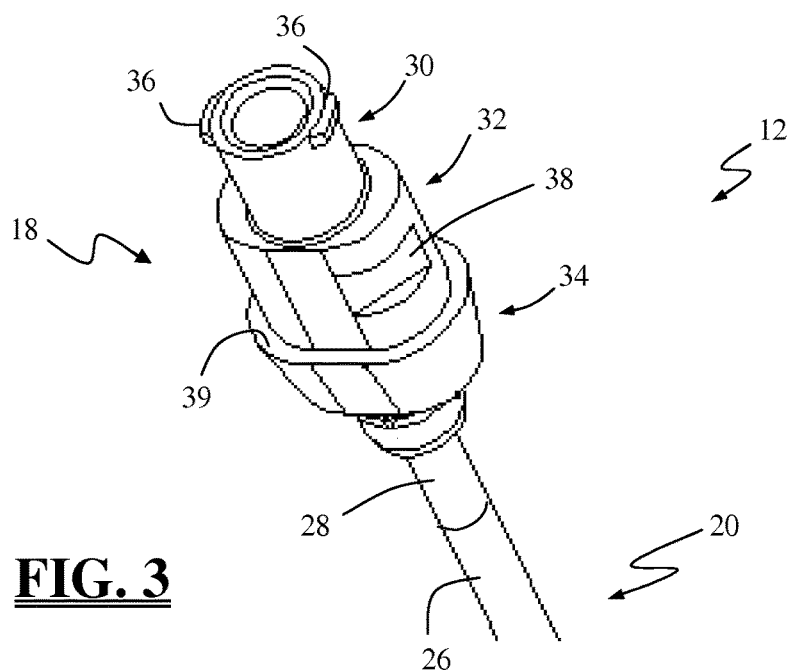
FIG. 3 is a perspective view of a coupling element forming part of the cannula of FIG. 2.

With reference to FIG. 3, coupling element 18 comprises a proximal region 30, a center section 32, and a base portion 34. Proximal region 30 is dimensioned to engage with the stylet 14 (described below). Proximal region 30 may include at least one tab member 36 that protrudes in a generally lateral direction from the proximal region 30. By way of example only, as shown in FIG. 3 proximal region 30 includes two tab members 36 positioned opposite one another and adjacent to first opening 22. As will be described in greater detail below, tab members 36 function to lock the cannula 12 and stylet 14 together. Center section 32 is dimensioned to be received within T-handle aperture 66 (FIG. 16) as described in further detail below. Center section 32 may be provided with at least one cutout 38 dimensioned to receive a locking mechanism 68 (FIG. 16) incorporated into T-handle 16 to secure the T-handle 16 to the cannula/stylet combination 15, or optionally to the cannula 12 only. The base 34 has a circumference that is greater than the circumference of center section 32, such that a ledge 39 is formed at the interface of center section 32 and the base portion 34. The ledge 39 engages the rim 72 of T-handle 16 so as to minimize potential stress on a T-handle locking mechanism 68 discussed below.

Figure 4:
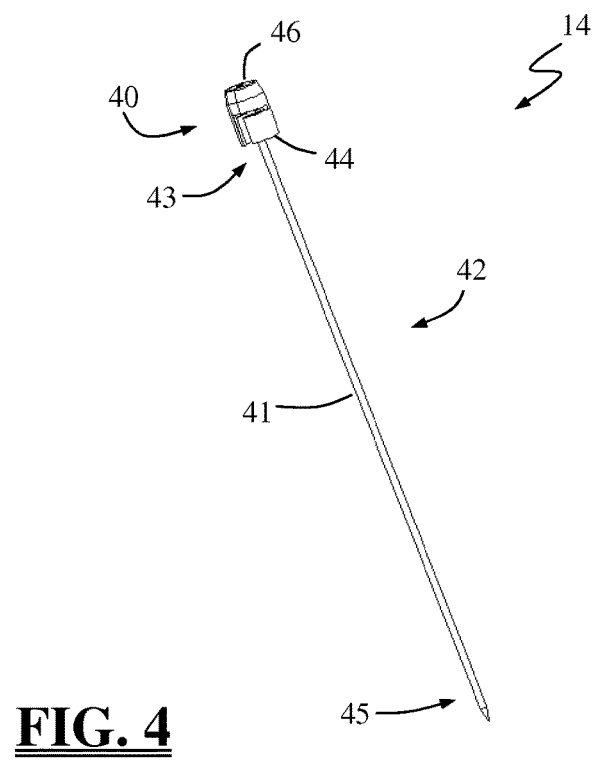
FIG. 4 is a perspective view of a stylet forming part of the pedicle access system of FIG. 1.
Figure 5:
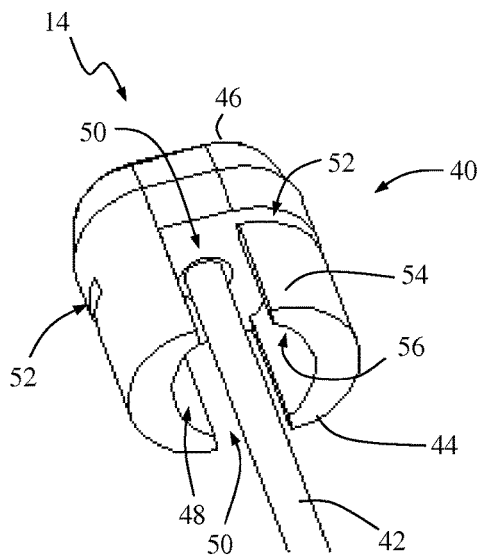
FIG. 5 is a perspective view of a locking cap forming part of the stylet of FIG. 4.

FIG. 4 illustrates an example of a stylet 14 forming part of the pedicle access system 10. Stylet 14 includes a locking cap 40 and a needle element 42. Locking cap 40 has a similar size and shape to center section 32, and is similarly dimensioned to be received within T-handle aperture 66, discussed below. Locking cap 40 includes a distal end 44 and a proximal end 46. As illustrated in FIG. 5, locking cap 40 includes a generally cylindrical aperture 48 having an opening at distal end 44 and extending in a proximal direction at least partially the length of locking cap 40. Generally cylindrical aperture 48 is dimensioned to receive the generally cylindrical proximal region 30 of cannula 12. Furthermore, locking cap 40 includes at least one longitudinal channel 50 (defined by an axis extending through the proximal and distal ends 46, 44 respectively) and at least one lateral channel 52 extending generally perpendicularly from longitudinal channel 50. Longitudinal channel 50 and lateral channel 52 each extend from an exterior surface 54 through an interior surface 56 into aperture 48. Preferably, the number of longitudinal channels 50 and lateral channels 52 correspond to the number of tab members 36 on cannula 12. By way of example only (and as shown in FIGS. 3-5), cannula 12 includes two tab members 36 and stylet 14 includes two longitudinal channels 50 and two lateral channels 52.

Figure 12:
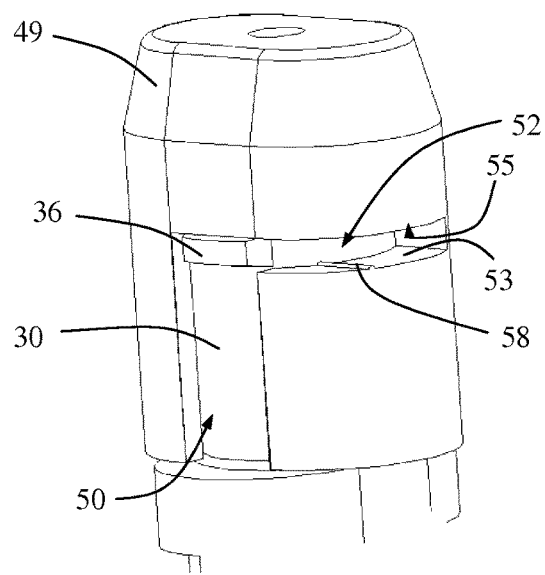
FIG. 12 is perspective view of the locking cap of the fully inserted stylet of FIG. 11, shown in an unlocked position.
Figure 13:
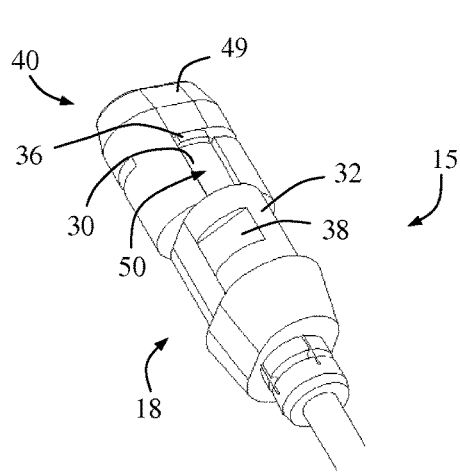
FIG. 13 is a perspective view of the cannula and stylet combination in the unlocked position of FIG. 11.

Longitudinal channel 50 initiates at the distal end 46 and has a length corresponding to the length of the generally cylindrical 48. Lateral channel 52 initiates at the proximal end of longitudinal channel 50 and extends generally perpendicularly therefrom such that together the longitudinal and lateral channels 50, 52 form a generally half-T shape. Longitudinal channel 50 and lateral channel 52 function to interact with the tab 36 on cannula 12, so as to lock the stylet 14 and cannula 12 together. Longitudinal channel 50 has a width dimension sufficient to accommodate the length of tab member 36 and lateral channel 52 has a height dimension sufficient to accommodate the height of tab member 36 (best viewed in FIG. 12). A ridge 58 (shown in FIG. 12) may be positioned along the distal-most edge 53 and/or proximal-most edge 55 of the lateral channel 52 to engage with tab member 36 and provide a locking means for the cannula/stylet combination 15. Additionally, a portion of exterior surface 54 adjacent to proximal end 46 may comprise a ramped surface 49 such that the circumference of distal end 44 is slightly greater than the circumference of proximal end 46, so as to facilitate engagement with the T-handle 16.

Figure 6:
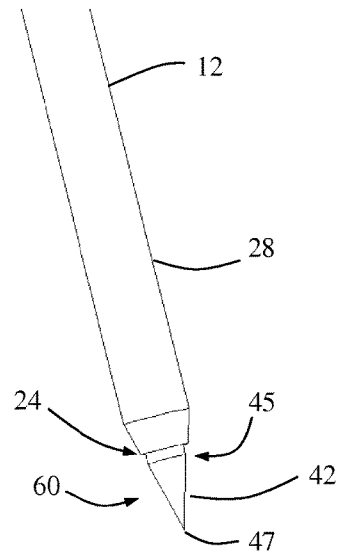
FIG. 6 is a perspective view of the distal portion of the stylet of FIG. 4 protruding from the distal region of the cannula of FIG. 2.

The needle element 42 comprises an elongated shaft 41 having a proximal region 43 and a distal region 45. The proximal region 43 may be attached to the interior of locking cap 40 between proximal end 46 and aperture 48. Elongated shaft 41 extends distally from proximal region 43 with a significant portion protruding generally perpendicularly from the opening of aperture 48. Needle element 42 is dimensioned to be inserted through the interior lumen of cannula 12. The distal region 45 generally includes a distal portion of elongated shaft 41 and a shaped tip 47 having any form or shape capable of being driven into the pedicle to create a pilot hole. By way of example only, shaped tip 47 may have a beveled or double diamond form. As illustrated in FIG. 6, when needle element 42 is fully inserted into cannula 12, at least a portion of distal region 45 (including shaped tip 47) may protrude slightly from the second opening 24 of cannula 12. Due to the insulated nature of cannula 12, the portion of needle element 42 that protrudes from cannula 12 effectively constitutes a stimulation region 60. The stimulation region 60 may include the distal region 45 and/or the shaped tip 47.

Figure 7:
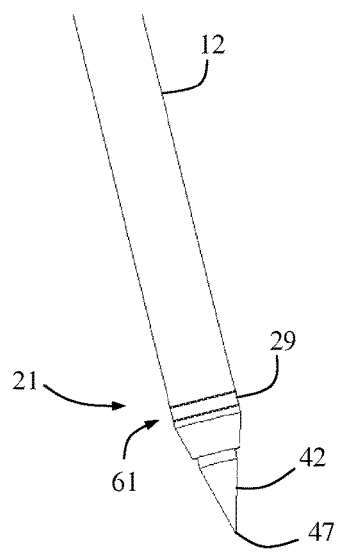
FIG. 7 is a perspective view of the distal portion of the stylet of FIG. 4 protruding from the distal region of the cannula of FIG. 2, with the distal region of the cannula having an uninsulated portion.
Figure 8:
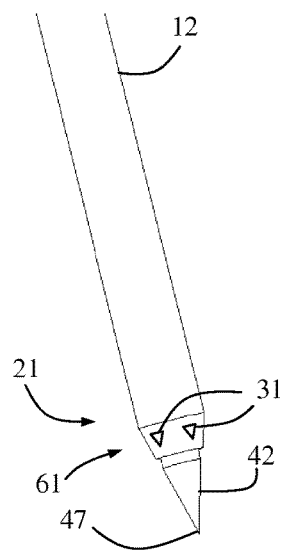
FIG. 8 is a perspective view of the distal portion of the stylet of FIG. 4 protruding from the distal region of the cannula of FIG. 2, with the distal region of the cannula having a directional electrode.

According to a further aspect of the present invention, any part of the needle element 42 (e.g. the elongated shaft 41, distal region 45 and/or shaped tip 47) may be provided with a coating to insulate and therefore limit or reduce the stimulation region 60 to a desired configuration. For example, the distal tip 47 may have an insulation coating to effectuate a stimulation region 60 consisting of the portion of the distal region 45 of the needle element 42 between the insulated cannula 12 and the insulated distal tip 47. Alternatively, the entirety of needle element 42 may be provided with an insulative coating and the distal region 21 of cannula 12 may be provided with (for example) one or more uninsulated portions 29 (FIG. 7) and/or one or more directional electrodes 31 (FIG. 8) forming a stimulation region 61. These alternative arrangements serve to mitigate an apparent phenomenon in which certain geometries (e.g. points and edges) tend to generate significantly higher current densities and therefore are much more efficient at exciting a nearby nerve, even through bone tissue. As a result, instrumentation having these geometries may show a lower stimulation threshold (and thus causing an EMG monitoring system to indicate a breach in an intact pedicle) unless this phenomenon is otherwise compensated for.

Needle element 42 may be composed of a conductive material, such as metal. Alternatively, needle element 42 may be composed of a non-conductive material with one or more embedded conductive elements at or near the distal end (e.g. distal region 45 and/or shaped tip 47) capable of being communicatively linked with a pedicle integrity testing system.

Figure 9:
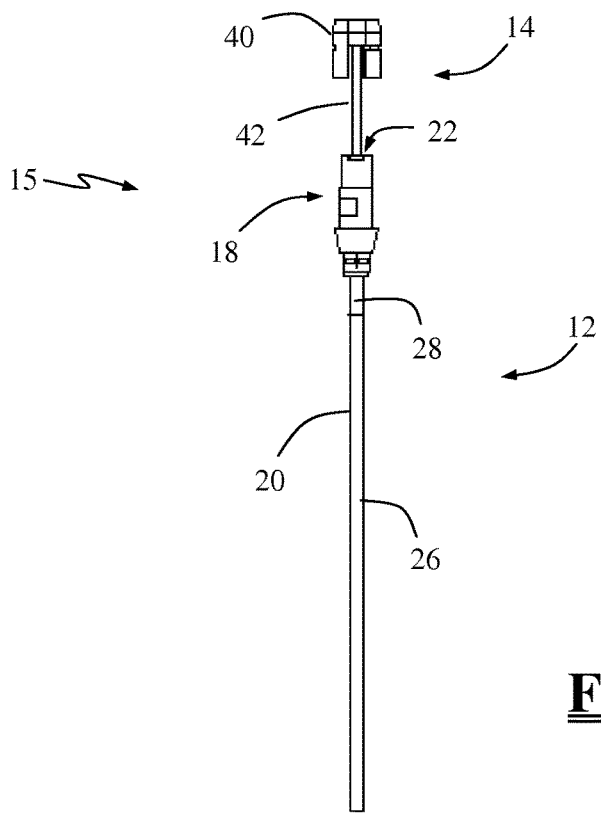
FIGS. 9-10 are plan and perspective views, respectively, of the stylet of FIG. 4 partially inserted into the cannula of FIG. 2.
Figure 10:
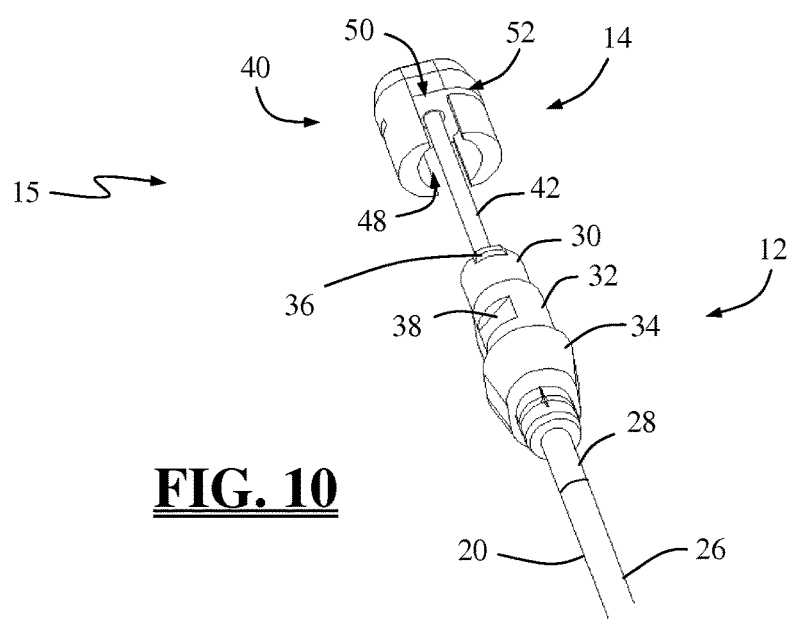
Figure 11:
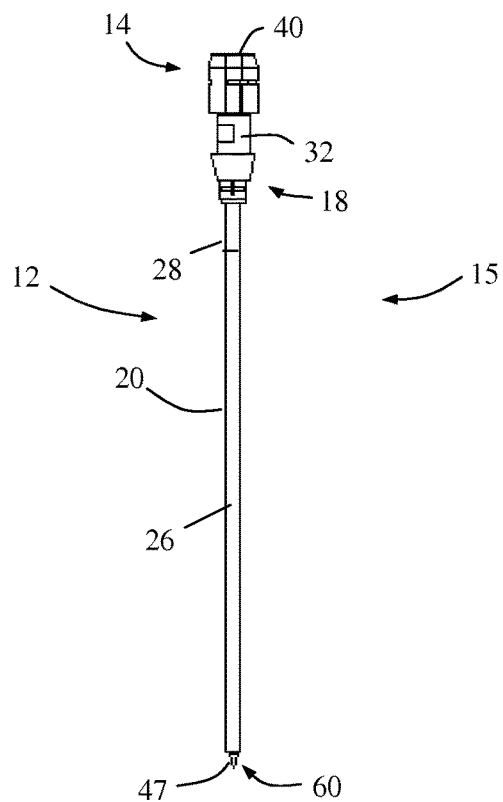
FIG. 11 is a is a plan view of the stylet of FIG. 4 fully inserted into the cannula of FIG. 2 in an unlocked position.
Figure 14:
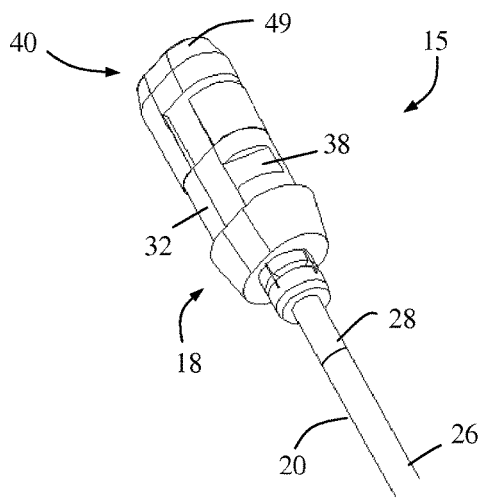
FIGS. 14-15 are perspective and plan views, respectively, of the cannula and stylet combination of FIG. 13 in the locked position.
Figure 15:
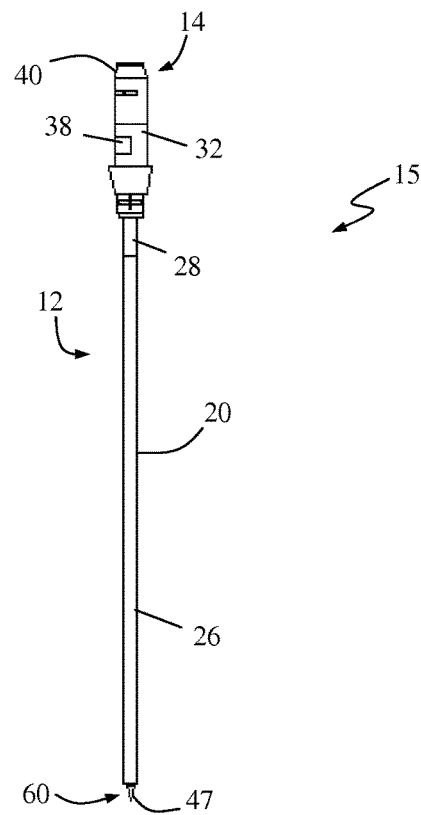

FIGS. 9-15 illustrate the formation of the cannula/stylet combination 15. In FIGS. 9-10 stylet 14 is introduced into cannula 12. Needle element 42 of stylet 14 is inserted into the interior lumen of cannula 12 through the first opening 22 of coupling element 18. The locking cap 40 of stylet 14 is positioned such that its longitudinal channels 50 are aligned with the tab members 36 of cannula 12. The proximal region 30 of cannula 12 is received into the aperture 48 of locking cap 40, and the tab members 36 pass through the longitudinal channels 50 as insertion of needle element 42 progresses. Insertion is complete when the proximal portion 30 is fully received by aperture 48, leaving the locking cap 40 in the "unlocked" position illustrated in FIGS. 11-13. As mentioned above, the distal region 45 of needle element 42 including shaped tip 47 (and the stimulation region 60) may protrude from the second opening 24 of the elongated shaft 20 of cannula 12 when stylet 14 is fully inserted, shown in FIG. 11. In the unlocked position, tab members 36 are positioned at the proximal end of longitudinal channels 50 where the channels intersect lateral channels 52. At this point, the corresponding shapes of the locking cap 40 of stylet 14 and center section 32 of cannula 12 are out of alignment. To lock stylet 14 in place and complete the combination, the locking cap 40 is rotated until it is aligned with the center section 32 as illustrated in FIGS. 14-15. As the lateral channels 52 rotate around the tab members 36, ridges 58 come into contact with the tab members 36. The ridges may not pass the tab members 36 if the locking cap 40 is not rotated with enough force to deform the ridges 58. Once the ridges 58 have deformed, the rotation may continue towards the final position. The locking cap 40 and center section 32 become aligned and the ridges 58 may clear the tab members 36 and regain their original forms, thereby preventing inadvertent rotation of the locking cap 40 back to the unlocked position.

Figure 16:
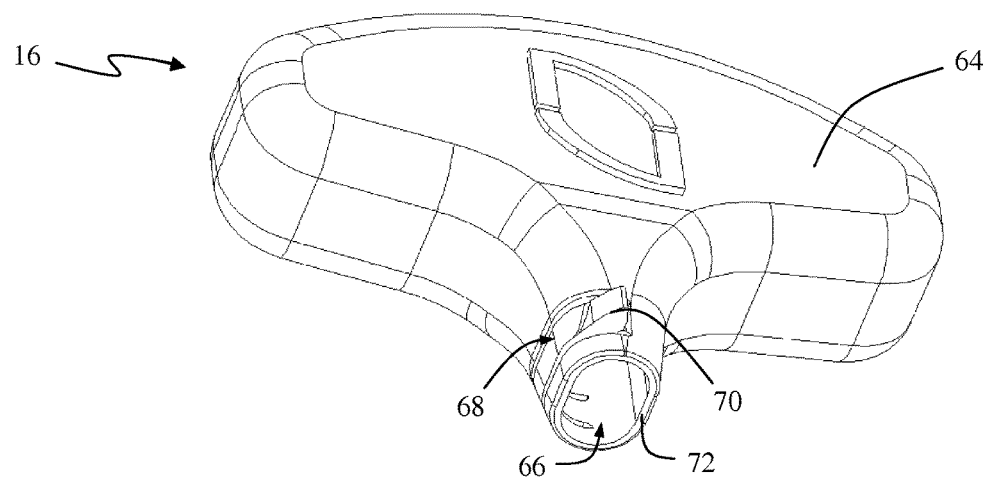
FIGS. 16-17 are perspective views of a T-handle forming part of the pedicle access system of FIG. 1.
Figure 17:
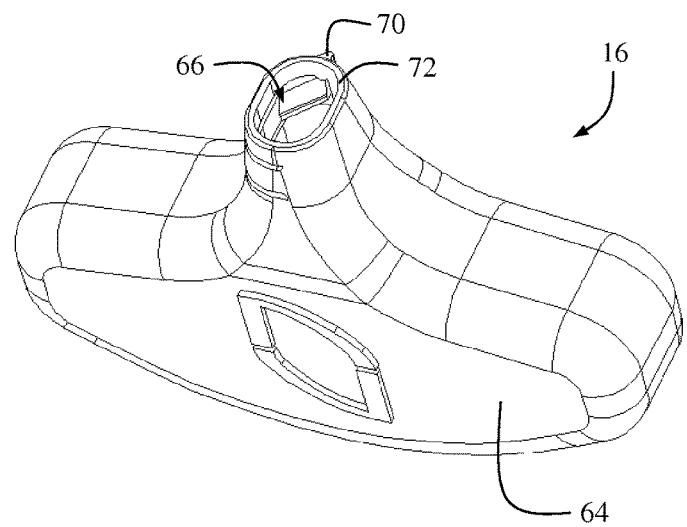
Figure 18:
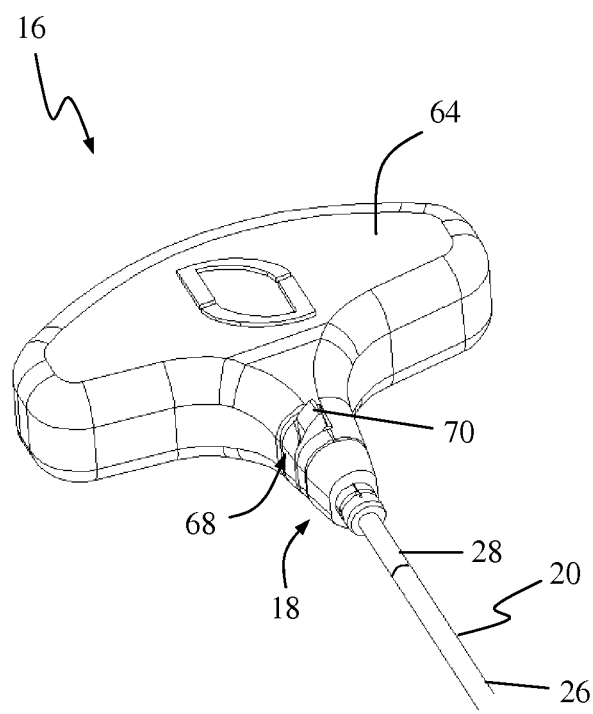
FIG. 18 is a perspective view of the pedicle access system of FIG. 1 with the cannula and stylet combination of FIG. 13 fully inserted and locked in the T-handle.

FIG. 16 illustrates an example of a T-handle 16 forming part of the pedicle access system 10. T-handle 16 includes a grip region 64, an aperture 66 for engaging the cannula 12 or cannula/stylet combination 15, and a locking mechanism 68 for securing the T-handle to the cannula 12. Grip region 64 may be provided in any number of suitable shapes and sizes that may aid the user in holding and manipulating the pedicle access system 10 during use. The T-handle aperture 66 is dimensioned to snugly receive both the locking cap 40 and center section 32 when they are aligned in the locked position as described above. The locking mechanism 68 preferably comprises a lever having one end that is integrated into the aperture wall and a free end 70 extending therefrom. The majority of the locking mechanism 68 (excluding free end 70) may comprise the same thickness as the aperture wall and does not protrude, interiorly or exteriorly, from the aperture wall. In its "natural" state, the interior surface of free end 70 protrudes into the aperture 66 space. The interior surface of free end 70 is dimensioned to engage the cutout 38 in the center section 32 of cannula 12. Furthermore, as illustrated in FIG. 17, the interior surface of free end 70 may be slightly ramped, such that the edge further from the aperture opening protrudes further into the aperture than the edge closer to the aperture opening. The ramped portion works in concert with the ramped surface 49 at the proximal end 46 of locking cap 40 to force the free end 70 out of its natural state as the locking cap 40 of stylet 14 and center section 32 of cannula 12 are received into the T-handle aperture 66. When the locking cap 40 and center section 32 are fully inserted into the T-handle aperture 66, as illustrated in FIG. 18, the interior surface of free end 70 aligns with the cutout 38 in the center section 32 and free end 70 returns to its natural state, thus locking the T-handle 16 to the cannula 12. Furthermore, as the locking cap 40 and center section 32 are fully inserted into the T-handle aperture 66, the ledge 39 engages the rim 72. This interaction functions to minimize potential stress on the T-handle locking mechanism 68 by increasing the surface area that receives force applied by the user. To remove the T-handle 16, the free end 70 may be lifted to disengage with the cutout 38, and the T-handle may be pulled off. Optionally, T-handle 16 may be cannulated (not shown) such that an interior lumen extends from an opening on the top of the handle into the aperture 66.

Figures 19, 20:
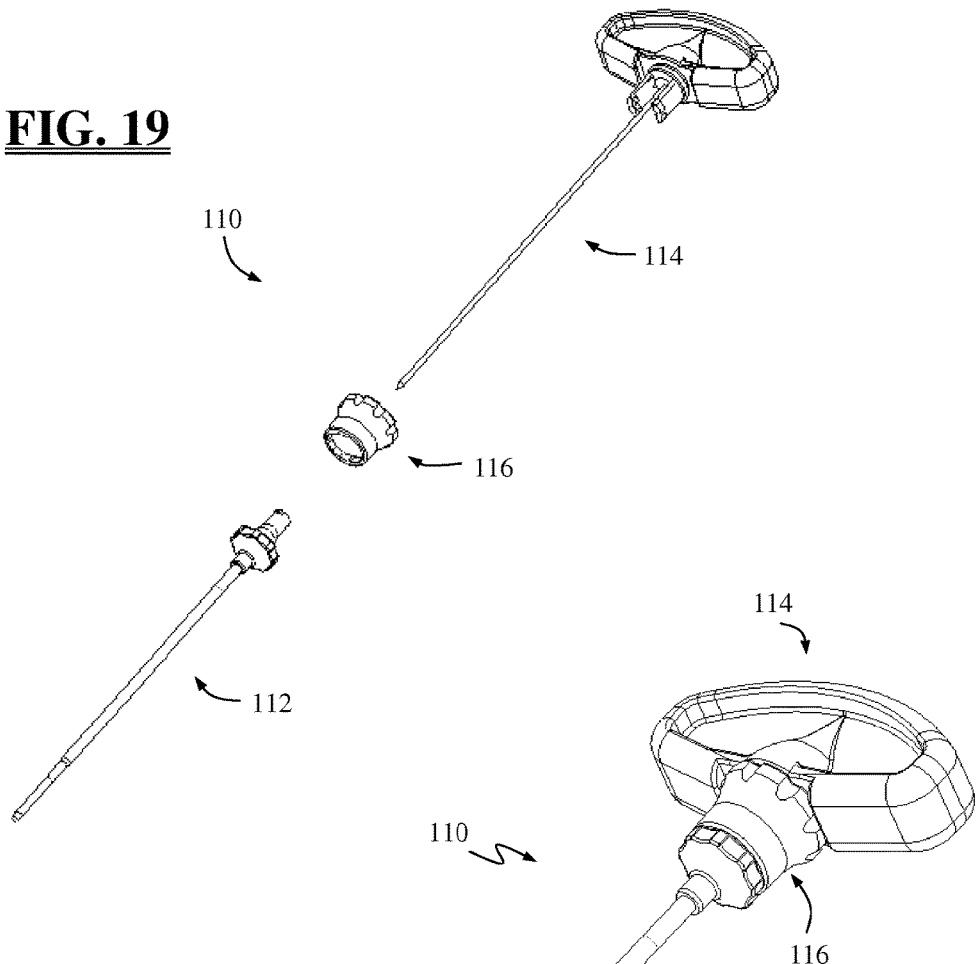
FIG. 19 is an exploded perspective view of a pedicle access system according to an alternative embodiment of the present invention.
FIG. 20 is a perspective view of the assembled pedicle access system of FIG. 19.

FIGS. 19-20 illustrate an example of a pedicle access system 110 according to an alternative embodiment of the present invention. The pedicle access system 110 includes a cannula 112, a stylet 114, and a lock collar 116. As described above in relation to pedicle access system 10, pedicle access system 110 may be used to percutaneously approach the pedicle, initiate pilot hole formation, and conduct a stimulation signal to the target site for the purposes of performing a pedicle integrity assessment during formation of the pilot hole. To do this, the cannula 112 and stylet 114 may be lockingly mated and inserted through an operating corridor to the pedicle target site, using the handle portion 140 of the stylet 114 to facilitate easy movement and positioning of pedicle access system 110. The pedicle access system 110 may be driven into the bone at the target site to form a pilot hole while a stimulation signal is applied and conducted to the target site to assess the integrity of the pedicle during hole formation. As shown and described herein, the cannula 112 and stylet 114 are generally cylindrical in shape. However, it should be understood that cannula 112 and stylet 114 may be provided in any suitable shape having any suitable cross-section (e.g. generally oval or polygonal) without deviating from the scope of the present invention.

Figure 21:
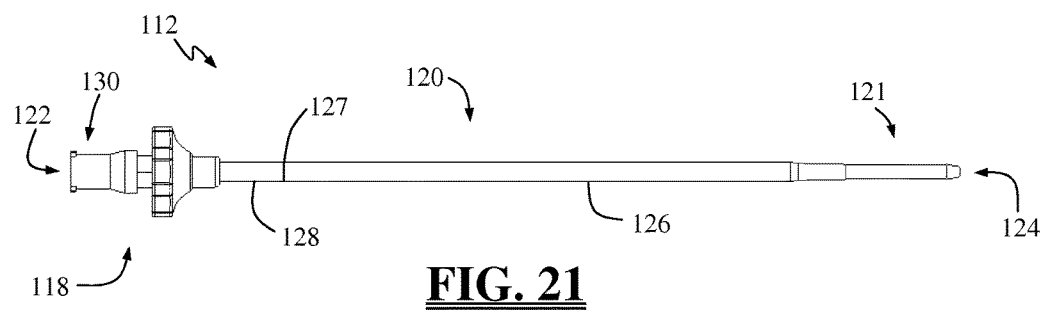
FIGS. 21-22 are plan and perspective views, respectively, of a cannula forming part of the pedicle access system of FIG. 20.
Figure 22:
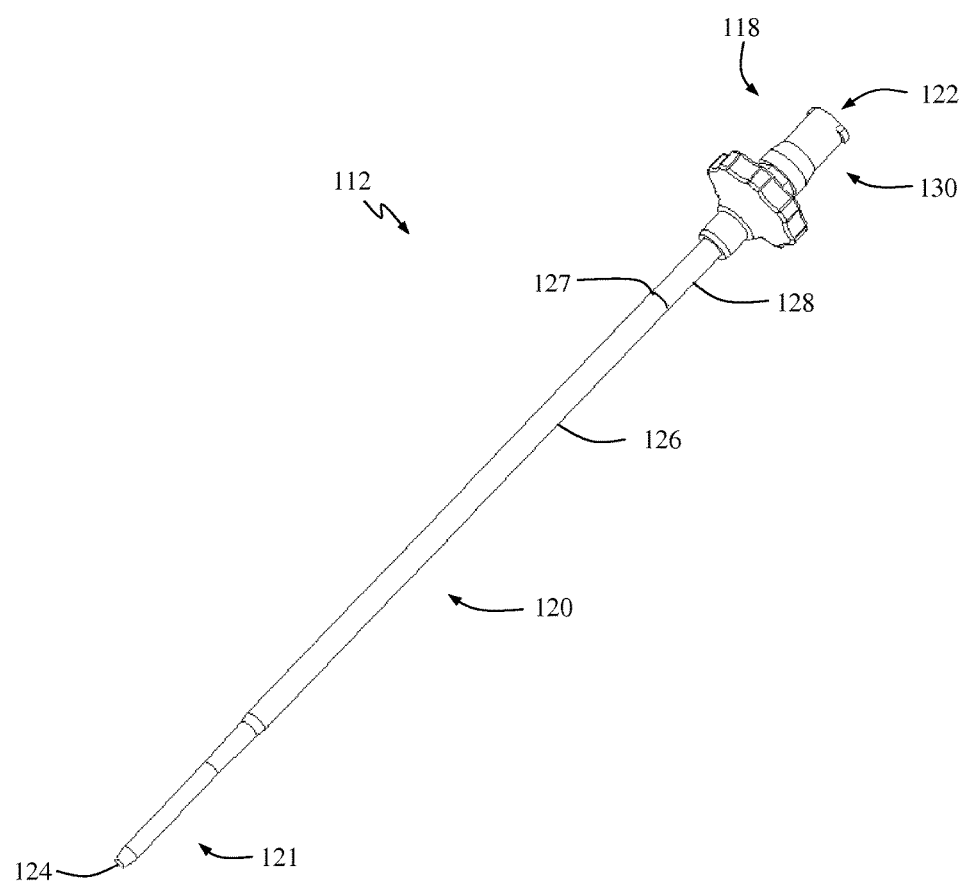

FIGS. 21-22 illustrate an example of a cannula 112 forming part of pedicle access system 110. Cannula 112 includes a coupling element 118 and an elongated shaft 120. An interior lumen extends through the cannula 112 from a first opening 122 located at a proximal region 130 of the coupling element 118 to a second opening 124 located at a distal end 121 of the elongated shaft 120. Elongated shaft 120 may be composed of any conductive material such as metal, for example. A polymeric coating may be provided on a substantial portion of the exterior surface of elongated shaft 120 such that elongated shaft 120 comprises an insulated portion 126 and an uninsulated portion 128 (the edge of the coating and thus the boundary between portions 126, 128 represented by callout 127 in FIGS. 21-22). Elongated shaft 120 may include any number of diameter changes incorporated along its length without deviating from the scope of the present invention. In the alternative, elongated shaft 120 may be provided with a uniform diameter along its length.

Figure 23:
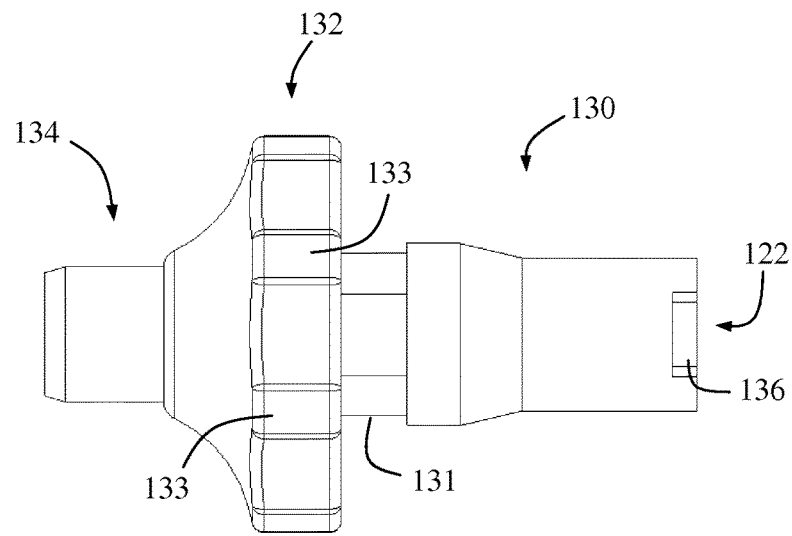
FIGS. 23-24 are plan and perspective views, respectively, of a coupling element forming part of the cannula of FIG. 21.
Figure 24:
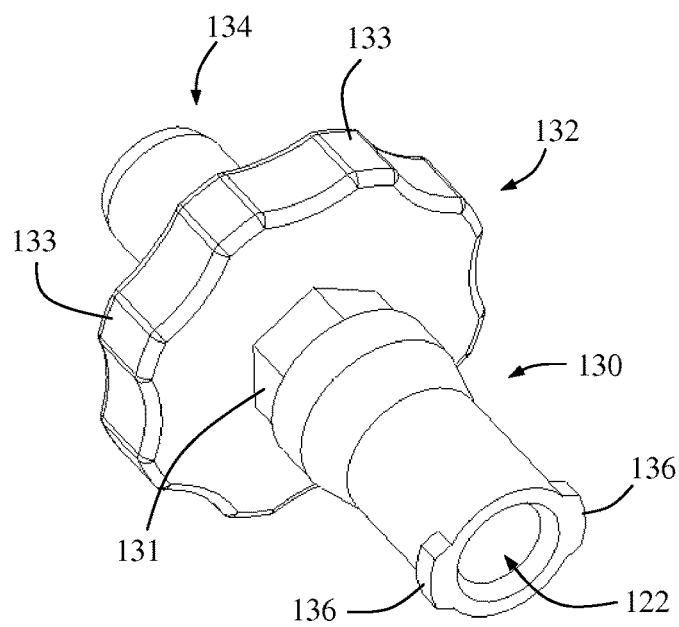

With reference to FIGS. 23-24, coupling element 118 comprises a proximal region 130, a center section 132, and a distal portion 134. Proximal region 130 includes an engagement region 131 dimensioned to engage with the handle portion 140 of the stylet 114 (as described in further detail below). The engagement region 121 may be provided in any suitable geometric configuration to allow for secure mating with the engagement tabs 144 of the handle 140. By way of example only, the coupling element 118 is shown in FIGS. 23-24 having a hexagonal engagement region 131, however other shapes are possible. Proximal region 130 may include at least one tab member 136 that protrudes in a generally lateral direction from the proximal region 130. By way of example only, as shown in FIG. 24 proximal region 130 includes two tab members 136 positioned opposite one another and adjacent to first opening 122. Tab members 136 may be utilized to attach supplemental instruments and/or apparatuses to the cannula 112. Center section 132 may be provided with a diameter that is larger than the diameters of the proximal region 130 and distal portion 134, and may be provided with a plurality of ridges 133 and/or other features for the purpose of providing a suitable gripping area for a user. The distal portion 134 is dimensioned to engage with the elongated shaft 120 of the cannula 112.

Figure 25:
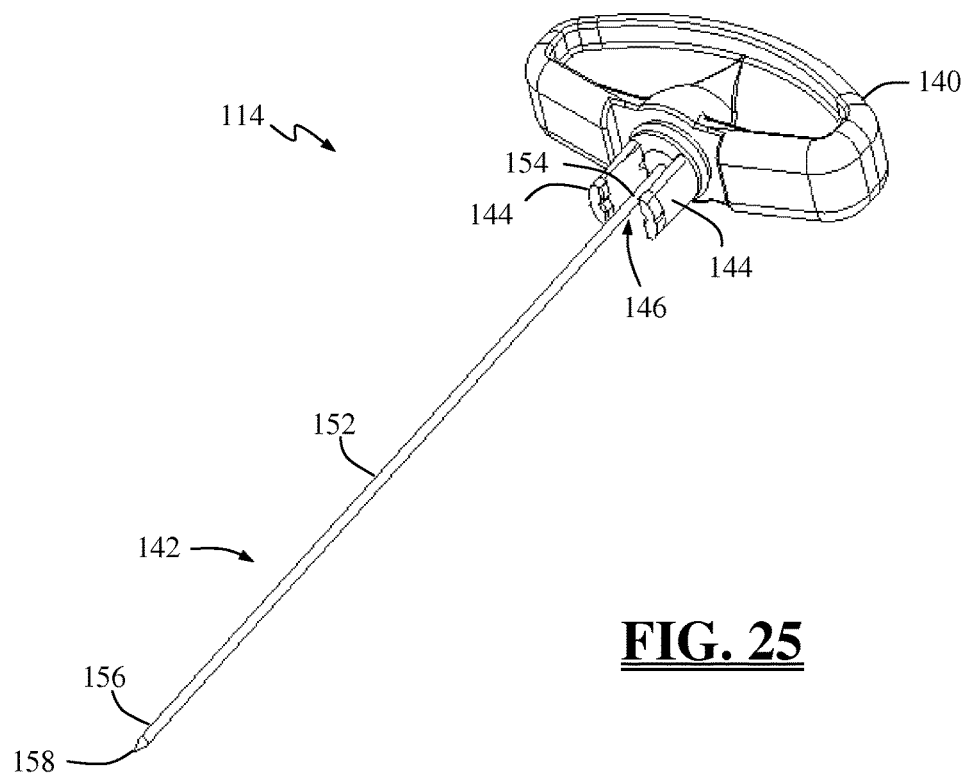
FIG. 25 is a perspective view of a stylet forming part of the pedicle access system of FIG. 20.
Figure 26:
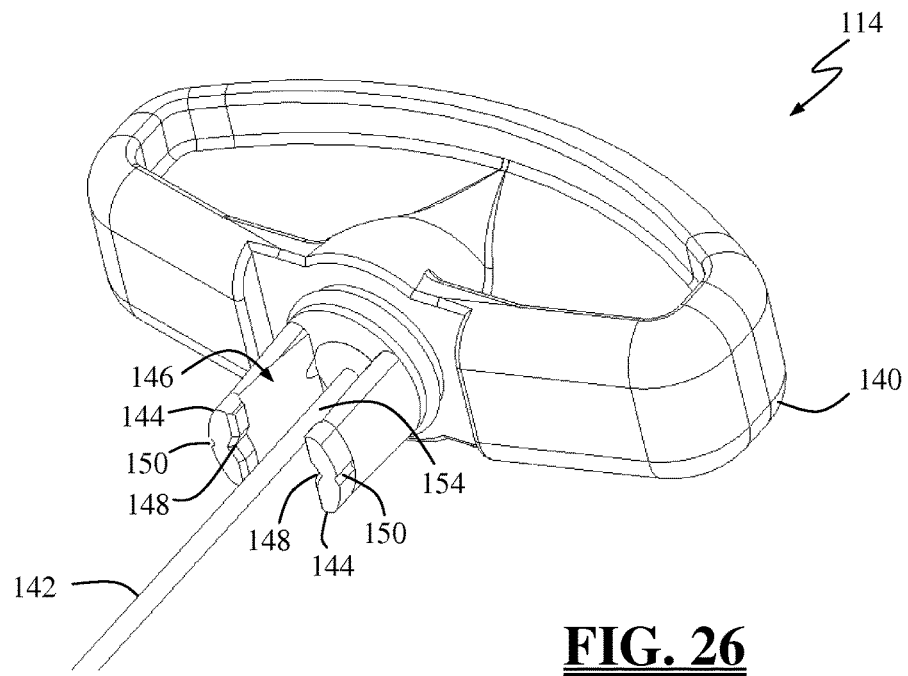
FIG. 26 is a perspective view of a handle forming part of the stylet of FIG. 25.

FIG. 25 illustrates an example of a stylet 114 forming part of the pedicle access system 110. Stylet 114 includes a handle portion 140 and a needle element 142. Handle portion 140 may (by way of example) resemble a T-handle for providing a user with a suitable gripping means. Handle portion 140 may be provided with a pair of engagement tabs 144 extending distally from handle portion 140. Engagement tabs 144 extend generally perpendicularly from the handle 140 and generally parallel to one another such that the engagement tabs 144 collectively form an interior space 146. Interior space 146 is dimensioned to receive the proximal region 130 of the coupling element 118 of the cannula 112. Each engagement tab 144 is provided with a medial (inwardly-facing) indentation 148 and a lateral (outwardlyfacing) indentation 150. Medial indentations 148 are dimensioned to engage the engagement region 131 of the coupling element 118, described above. For this reason, the medial indentations 148 may be provided with any geometry complementary to the shape of the engagement region 131 such that when mated, the engagement tabs 144 (via the medial indentations 148) will prevent movement of the engagement region 131, in effect locking the cannula 112 in place relative to the stylet 114. The lateral indentations 150 are dimensioned to interact with the first and second protrusions 170, 172 of the lock collar 116 described in further detail below.

Figure 27:
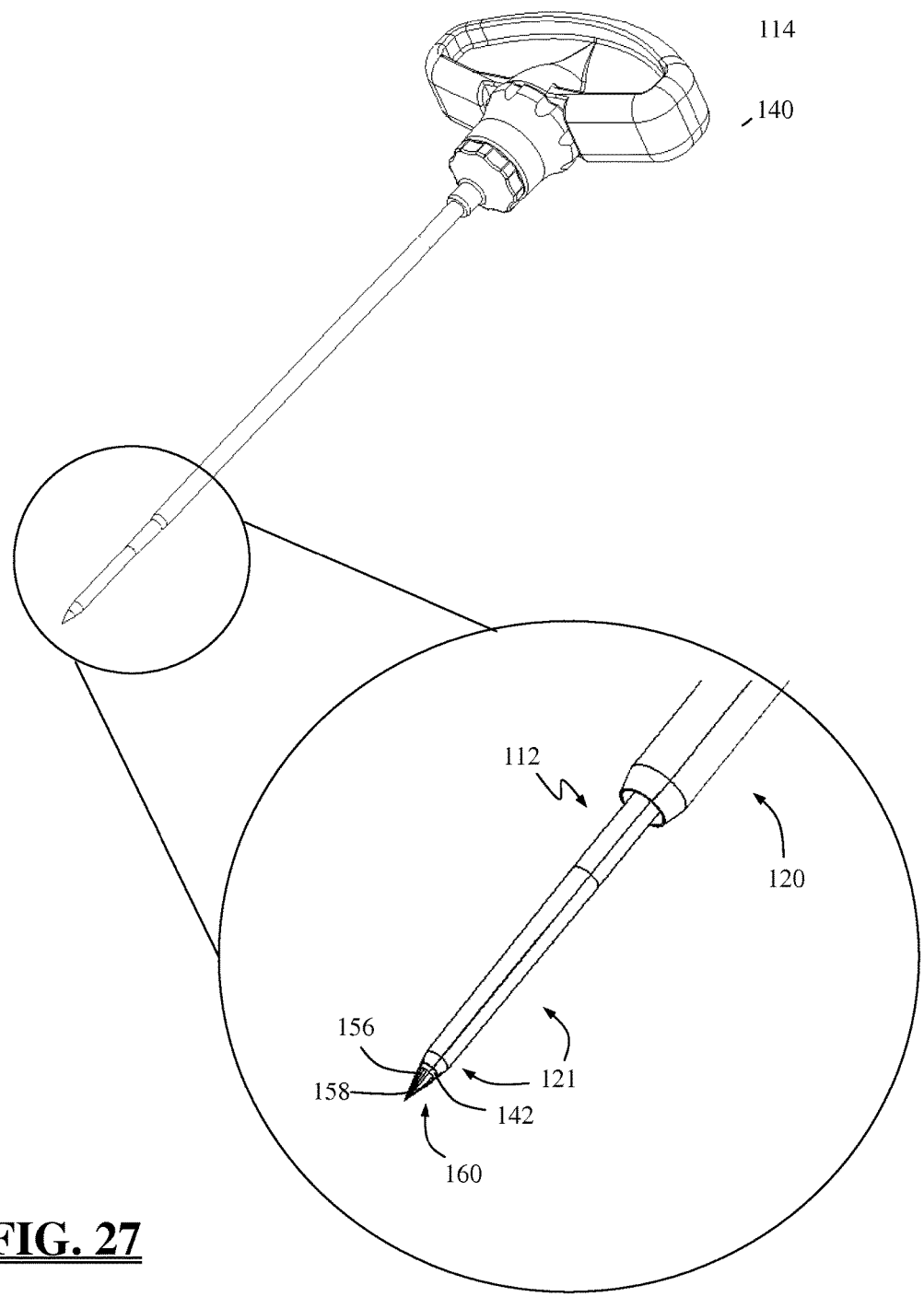
FIG. 27 is a perspective view of the pedicle access system of FIG. 20 including an enlarged view of a distal region thereof.

The needle element 142 comprises an elongated shaft 152 having a proximal region 154 and a distal region 156. The proximal region 154 may be attached to the interior of handle portion 140. Elongated shaft 152 extends distally from proximal region 154 and generally perpendicularly from the handle 140. Needle element 142 is dimensioned to be inserted through the interior lumen of cannula 112. The distal region 156 generally includes a distal portion of elongated shaft 152 and a shaped tip 158 having any form or shape capable of being driven into the pedicle to create a pilot hole. By way of example only, shaped tip 158 may have a beveled or double diamond form. As illustrated in FIG. 27, when needle element 142 is fully inserted into cannula 112, at least a portion of distal region 156 (including shaped tip 158) may protrude slightly from the second opening 124 of cannula 112. Due to the insulated nature of cannula 112, the portion of needle element 142 that protrudes from cannula 112 effectively constitutes a stimulation region 160. The stimulation region 160 may include the distal region 152 and/or the shaped tip 158.

According to a further aspect of the present invention, any part of the needle element 142 (e.g. the elongated shaft 152, distal region 156 and/or shaped tip 158) may be provided with a coating to insulate and therefore limit or reduce the stimulation region 160 to a desired configuration. For example, the distal tip 158 may have an insulation coating to effectuate a stimulation region 160 consisting of the portion of the distal region 156 of the needle element 142 between the insulated cannula 112 and the insulated distal tip 158. This coating serves to mitigate an apparent phenomenon in which certain geometries (e.g. points and edges) tend to generate significantly higher current densities and therefore are much more efficient at exciting a nearby nerve, even through bone tissue. As a result, instrumentation having these geometries may show a lower stimulation threshold (and thus causing an EMG monitoring system to indicate a breach in an intact pedicle) unless this phenomenon is otherwise compensated for.

Needle element 142 may be composed of any conductive material, such as metal. Alternatively, needle element 142 may be composed of a non-conductive material with one or more embedded conductive elements at or near the distal end (e.g. distal region 156 and/or shaped tip 158) capable of being communicatively linked with a pedicle integrity testing system.

Figure 28:
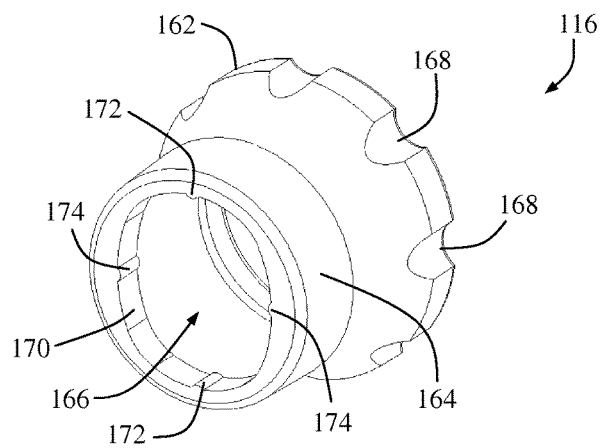
FIGS. 28-30 are perspective, top plan and bottom plan views, respectively, of a lock collar forming part of the pedicle access system of FIG. 20.
Figure 29:
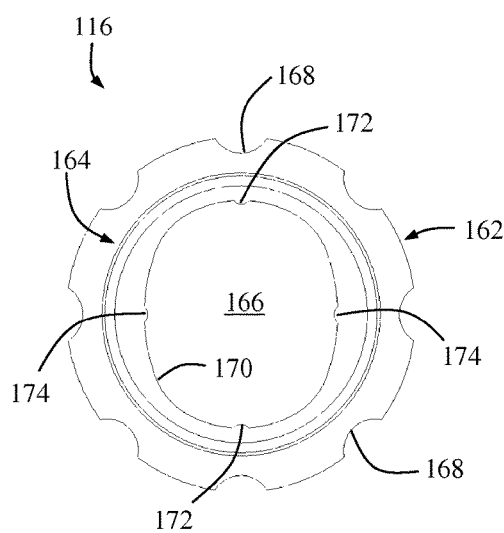
Figure 30:
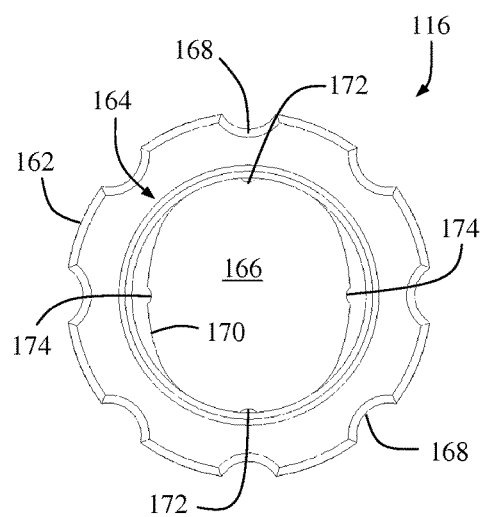
Figure 31:
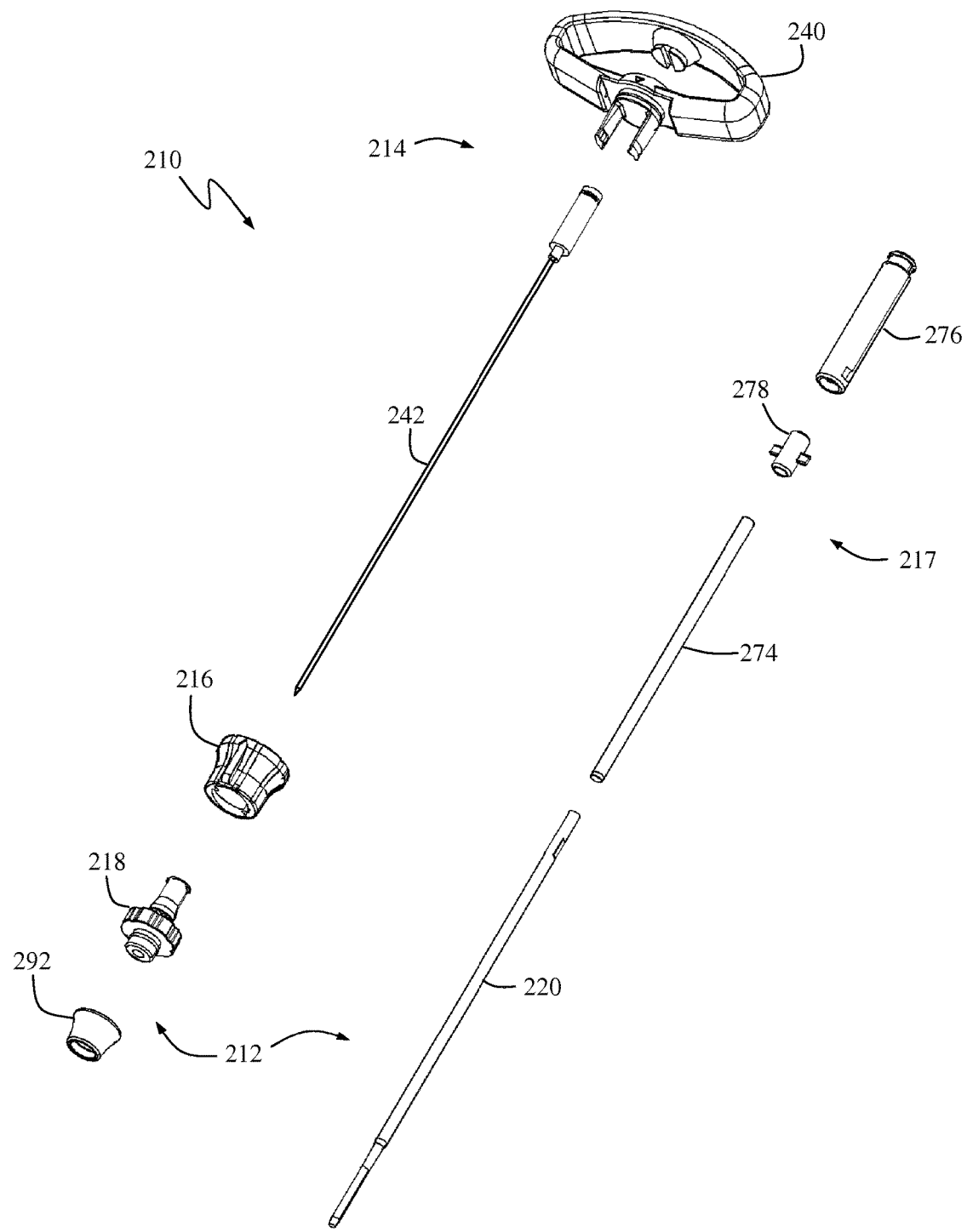
FIG. 31 is an exploded perspective view of a pedicle access system according to a further alternative embodiment of the present invention.

With reference to FIGS. 28-30, a lock collar 116 is provided to lockingly mate the cannula 112 and the stylet 114. Lock collar 116 has a generally cylindrical overall shape, and includes a proximal portion 162, a distal portion 164 and an interior lumen 166 extending therethrough. The proximal portion 162 may have a diameter greater than that of the distal portion 164 and is provided with a plurality of friction elements 168 to allow a user to grasp and turn the lock collar 116. The distal portion 164 includes a generally oval-shaped opening 170 providing access to the lumen 166.

The opening 170 further includes a pair of opposing first protrusions 172 and a pair of opposing second protrusions 174 located along the inside edge of opening 170. First protrusions 172 are located 180° from one another and are positioned at the long ends of the oval-shaped opening 170. Second protrusions 174 are positioned at the narrow sides of the oval-shaped opening 170 (and thus are located at 90° intervals from the first protrusions 172 and 180° from one another). First and second protrusions 172, 174 are each dimensioned to engage the lateral indentations 150 provided on the engagement tabs 144 of the handle 140, described above.

The interior lumen 166 is dimensioned to receive both of the engagement tabs 144 of the handle 140. Initially, the pedicle access system 110 of the present invention may be provided with the locking collar 116 attached to the stylet 114 in an initial position. This initial position is defined by the first protrusions 172 resting in the lateral indentations 150 of the engagement tabs 144 of the handle 140. Upon insertion of the needle element 142 into the cannula 112, the distal region 130 of the coupling element 118 of cannula 112 will enter the space 146 of the handle 140 such that the medial indentations 148 are aligned with (but not yet engaging) the engagement region 131 of the coupling element 118. At this point, a user would then rotate the lock collar 116 90° to a second position such that the second protrusions 174 rest in the lateral indentations 150. Due to the oval-shaped nature of the opening 170, upon rotation of the lock collar 116, the engagement tabs 144 will be forced toward one another, and the medial indentations 148 will come in contact with and positively engage the engagement region 131. As noted previously, this positive engagement prevents the cannula 112 from moving. At the same time, the lock collar 116 serves to lock the engagement tabs 114 in place, effectively locking the cannula 112 and the stylet 114 together. The pedicle access system 110 is now ready for use.

FIGS. 31-34 illustrate an example of a pedicle access system 210 according to a further alternative embodiment of the present invention. The pedicle access system 210 includes a cannula 212, a stylet 214, a lock collar 216 and a retractable insulation sheath 217. As described above in relation to pedicle access systems 10 and 110, pedicle access system 210 may be used to percutaneously approach the pedicle, initiate pilot hole formation, and conduct a stimulation signal to the target site for the purposes of performing a pedicle integrity assessment during formation of the pilot hole. To do this, the cannula 212 and stylet 214 may be lockingly mated and inserted through an operating corridor to the pedicle target site, using the handle portion 240 of the stylet 214 to facilitate easy movement and positioning of pedicle access system 210. The pedicle access system 210 may be driven into the bone at the target site to form a pilot hole while a stimulation signal is applied and conducted to the target site to assess the integrity of the pedicle during pilot hole formation. The retractable insulation sheath 217 functions to ensure maximum efficiency of the stimulation signal as by limiting or preventing shunting of the signal during pilot hole formation. As shown and described herein, the cannula 212, stylet 214 and retractable insulation sheath 217 are generally cylindrical in shape. However, it should be understood that cannula 212, stylet 214 and sheath 217 may be provided in any suitable shape having any suitable cross-section (e.g. generally oval or polygonal) without deviating from the scope of the present invention.

The retractable insulation sheath 217 functions to ensure maximum efficiency of the stimulation signal as by limiting or preventing shunting of the signal during pilot hole formation. With specific reference to FIGS. 32-34, this is accomplished by providing a tubular insulation member 274 slideably mated with a housing member 276 described in greater detail below. In an initial position (shown in FIGS. 33-34), the tubular insulation member 274 is fully extended such that it extends at least to the tip 258 of the stylet 214. Upon formation of a pilot hole in a pedicle (or other piece of bone), the stylet 214 will advance into the bone while the insulation sheath remains outside the bone (a position shown by way of example in FIG. 32). Due to the insulative properties of the sheath 217, the electrical current when supplied will be directed into the pilot hole by the uninsulated portion of the cannula 212 and stylet 214 while prevented from shunting outside of the hole by the sheath 217.

FIGS. 35-36 illustrate an example of a cannula 212 forming part of pedicle access system 210 of the present invention. Cannula 212 includes a coupling element 218 and an elongated shaft 220. An interior lumen extends through the cannula 212 from a first opening 222 located at a proximal region 230 of the coupling element 218 to a second opening 224 located at a distal end 221 of the elongated shaft 220. Elongated shaft 220 may be composed of any conductive material such as metal, for example. Elongated shaft 220 may include any number of diameter changes incorporated along its length without deviating from the scope of the present invention. In the alternative, elongated shaft 220 may be provided with a uniform diameter along its length.

Figure 37:
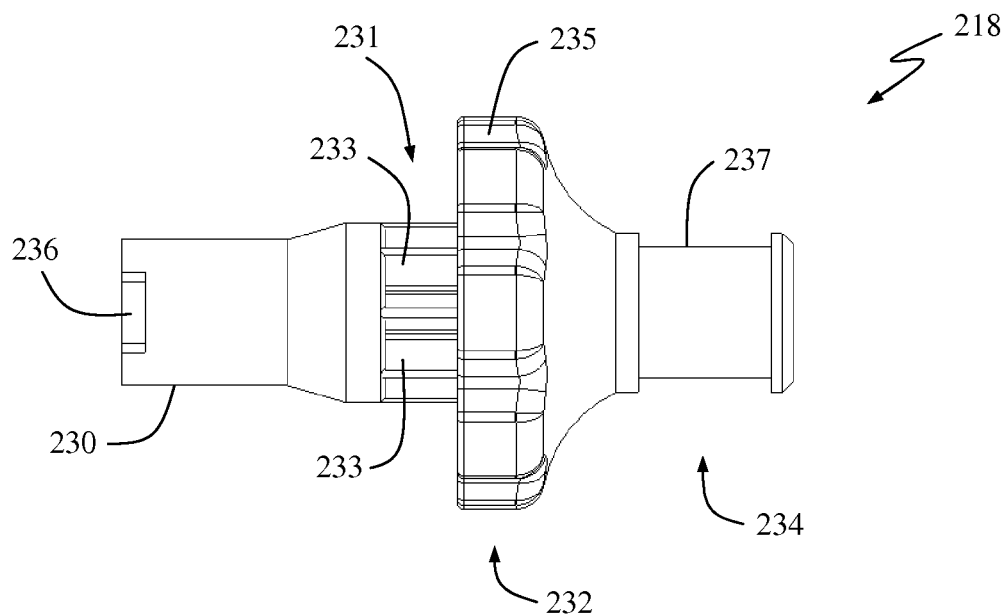
FIGS. 37-38 are side and perspective views, respectively, of a coupling element forming part of the cannula of FIG. 35.
Figure 38:
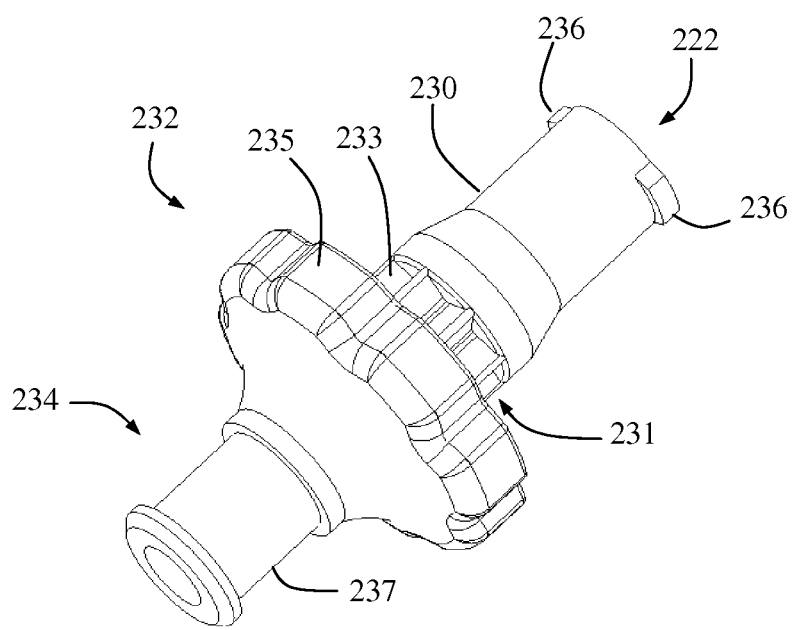

With reference to FIGS. 37-38, coupling element 218 comprises a proximal region 230, a center section 232, and a distal portion 234. Proximal region 230 includes an engagement region 231 dimensioned to engage with the handle portion 240 of the stylet 214 (as described in further detail below). The engagement region 231 may be provided in any suitable geometric configuration to allow for secure mating with the engagement tabs 144 of the handle 140. By way of example only, the coupling element 218 is shown in FIGS. 37-38 having a plurality of triangular-shaped indentations 233, however other shapes are possible. Proximal region 230 may include at least one tab member 236 that protrudes in a generally lateral direction from the proximal region 230. By way of example only, as shown in FIG. 38 proximal region 230 includes two tab members 236 positioned opposite one another and adjacent to first opening 222. Tab members 236 may be utilized to attach supplemental instruments and/or apparatuses to the cannula 212. Center section 232 may be provided with a diameter that is larger than the diameters of the proximal region 230 and distal portion 234, and may be provided with a plurality of ridges 235 and/or other features for the purpose of providing a suitable gripping area for a user. The distal portion 234 is dimensioned to engage with the elongated shaft 220 of the cannula 212 and may further be provided with a recess 237 for engagement with the sheath attachment element 292, described in further detail below.

Figure 39:
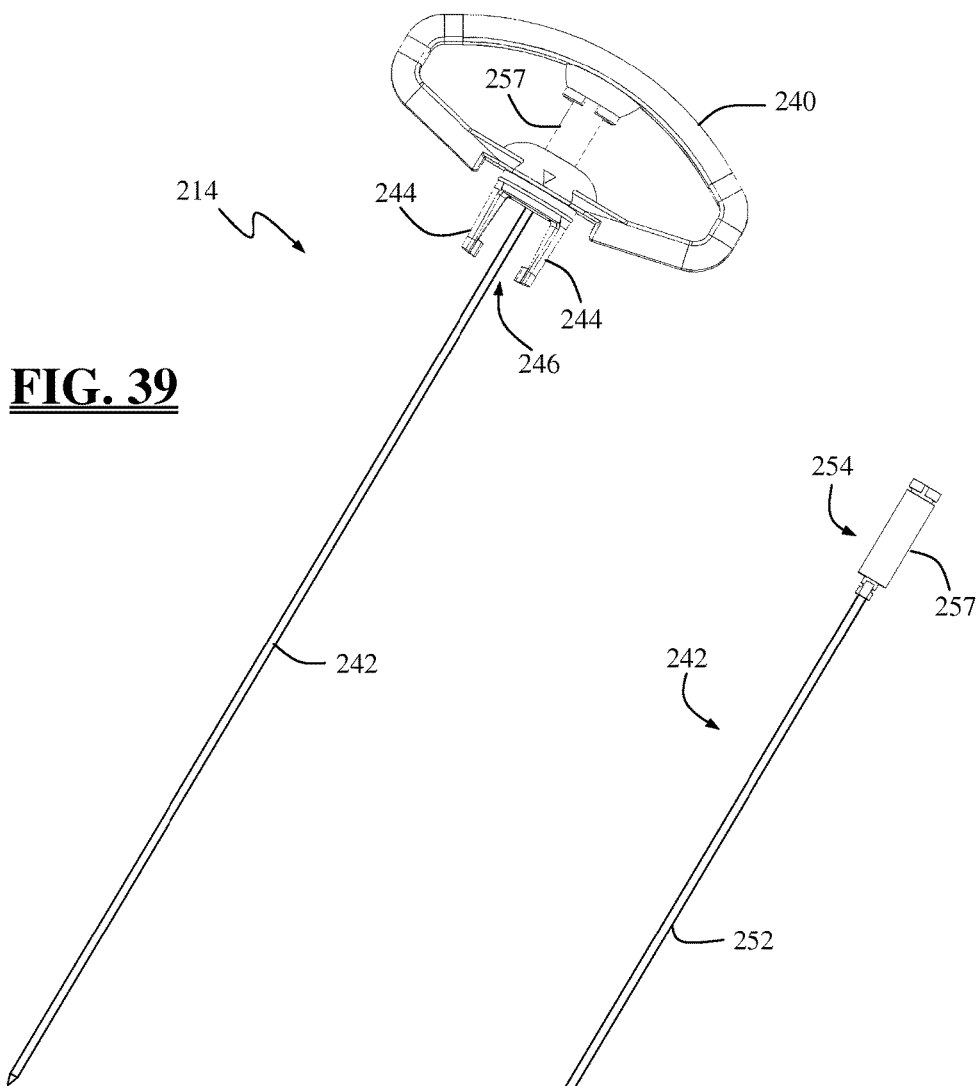
FIG. 39 is a perspective view of a stylet forming part of the pedicle access system of FIG. 31.
Figure 41:
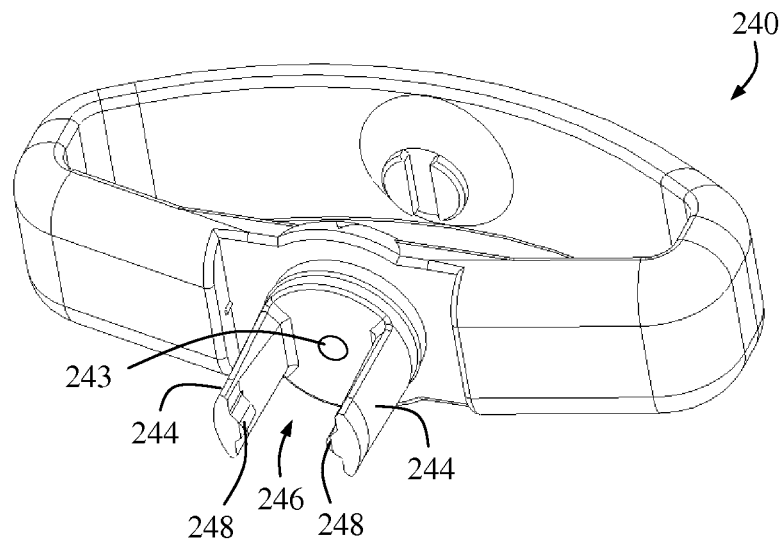
FIGS. 41-42 are perspective and plan views, respectively, of a handle forming part of the stylet of FIG. 39.
Figure 42:
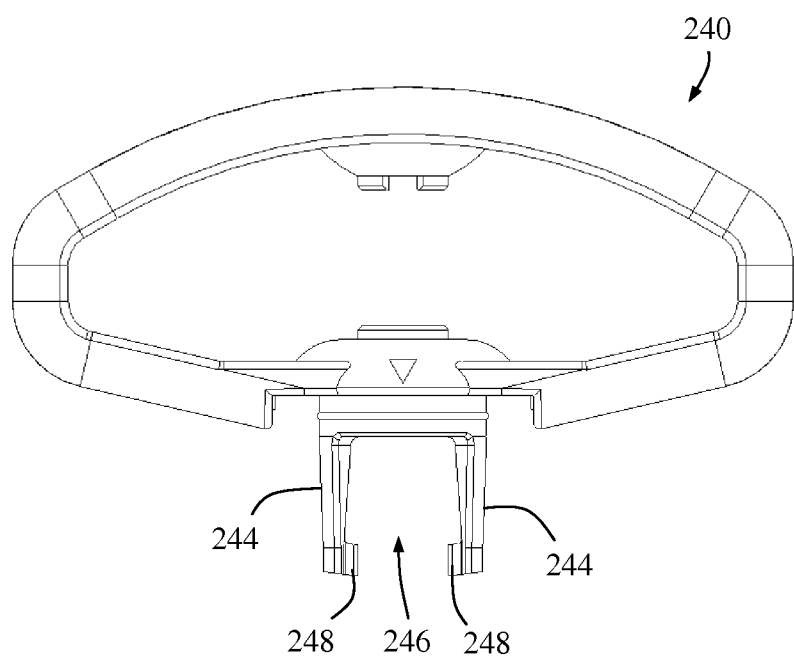

FIG. 39 illustrates an example of a stylet 214 forming part of the pedicle access system 210. Stylet 214 includes a handle portion 240 and a needle element 242. Referring to FIGS. 41-42, the handle portion 240 may (by way of example) resemble a T-handle for providing a user with a suitable gripping means. By way of example only, the handle portion 240 may have a substantially hollow interior that is not fully enclosed. Handle portion 240 includes an aperture 243 and a pair of engagement tabs 244 extending distally from handle portion 240. Aperture 243 is dimensioned to allow passage of the needle element 242 from the handle portion 240. Engagement tabs 244 extend generally perpendicularly from the handle 240 and generally parallel to one another such that the engagement tabs 244 collectively form an interior space 246. Interior space 246 is dimensioned to receive the proximal region 1230 of the coupling element 218 of the cannula 212. Each engagement tab 244 is provided with a medial (inwardly-facing) protrusion 248. Medial protrusions 248 are dimensioned to engage the engagement region 231 of the coupling element 218, described above. For this reason, the medial protrusions 248 may be provided with any geometry complementary to the shape of the engagement region 231 such that when mated, the engagement tabs 244 (via the medial protrusions 248) will prevent movement of the engagement region 231, in effect locking the cannula 212 in place relative to the stylet 214.

Figure 40:
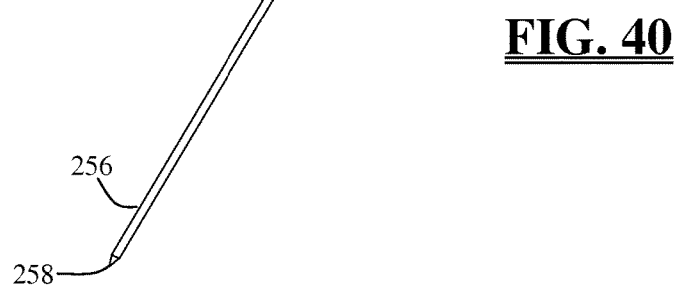
FIG. 40 is a perspective view of a needle forming part of the stylet of FIG. 39.

With reference to FIG. 40, the needle element 242 comprises an elongated shaft 252 having a proximal region 254 and a distal region 256. The proximal region 254 includes an attachment element 257 configured to attach to the interior of handle portion 240. The attachment element 257 is also configured to provide a point of contact for an electrical stimulation source (e.g. a clip attached to an electrical source). Elongated shaft 252 extends distally from proximal region 254 and generally perpendicularly from the handle 240 (and through aperture 243). Needle element 242 is dimensioned to be inserted through the interior lumen of cannula 212. The distal region 256 generally includes a distal portion of elongated shaft 252 and a shaped tip 258 having any form or shape capable of being driven into the pedicle to create a pilot hole. By way of example only, shaped tip 258 may have a beveled or double diamond form. When needle element 242 is fully inserted into cannula 212, at least a portion of distal region 256 (including shaped tip 258) may protrude slightly from the second opening 224 of cannula 212.

Needle element 242 may be composed of any conductive material, such as metal. Alternatively, needle element 242 may be composed of a non-conductive material with one or more embedded conductive elements at or near the distal end (e.g. distal region 256 and/or shaped tip 258) capable of being communicatively linked with a pedicle integrity testing system. Although shown as separate parts, the stylet 214 is preferably provided as a single unit, with the needle element 242 and attachment element 257 molded in place in the handle 240.

Figure 43:
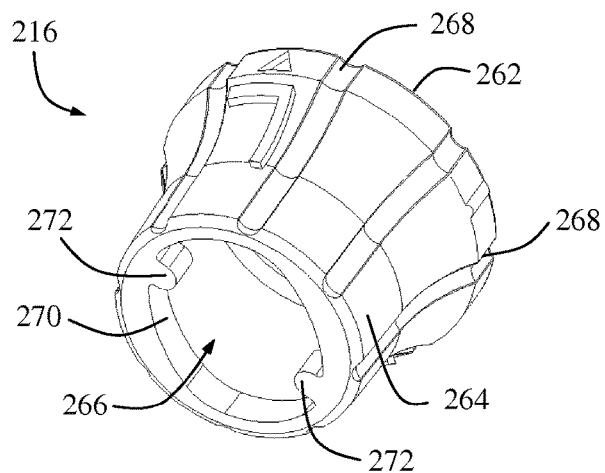
FIGS. 43-44 are perspective and plan views, respectively, of a lock collar forming part of the pedicle access system of FIG. 31.
Figure 44:
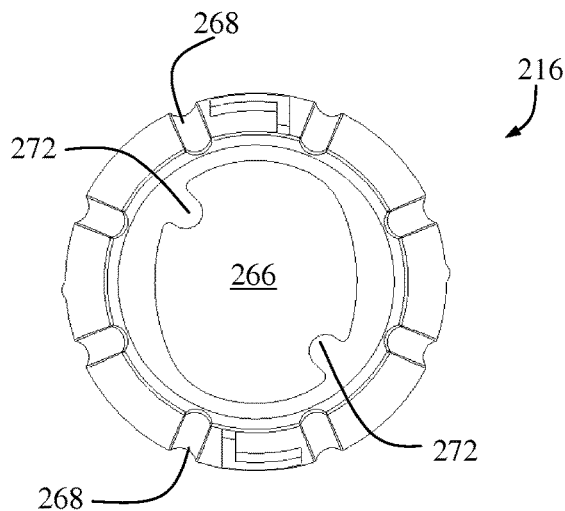

With reference to FIGS. 43-44, a lock collar 216 is provided to lockingly mate the cannula 212 and the stylet 214. Lock collar 216 has a generally cylindrical overall shape, and includes a proximal portion 262, a distal portion 264 and an interior lumen 266 extending therethrough. The proximal portion 262 may have a diameter greater than that of the distal portion 264 and is provided with a plurality of friction elements 268 to allow a user to grasp and turn the lock collar 216. The distal portion 264 includes a generally oval-shaped opening 270 providing access to the lumen 266. The opening 270 further includes a pair of opposing protrusions 272 located along the inside edge of opening 270. Protrusions 272 are located 180° from one another and are positioned approximately midway between the "long ends" and the "narrow sides" of the oval-shaped opening 270. Protrusions 272 are dimensioned to engage the sides of engagement tabs 244 of the handle 240, described above.

Figure 45:
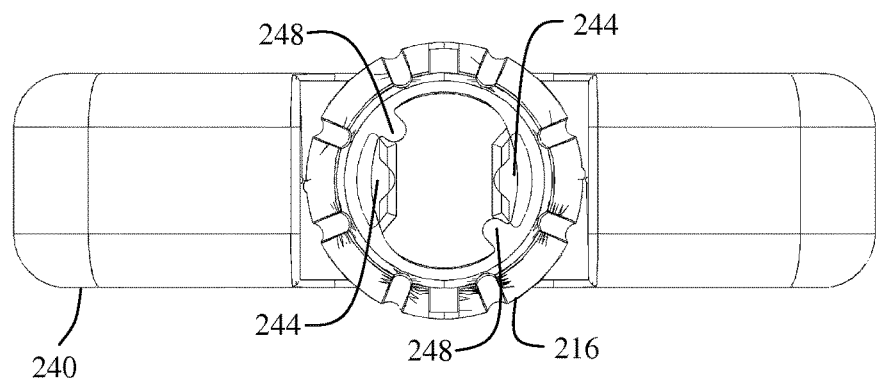
FIG. 45 is a bottom plan view of a handle of FIG. 46 in engagement with a lock collar of FIG. 43.

The interior lumen 266 is dimensioned to receive both of the engagement tabs 244 of the handle 240. Initially, the pedicle access system 210 of the present invention may be provided with the locking collar 216 attached to the stylet 214 in an initial position. This initial position is defined by the protrusions 272 resting alongside the engagement tabs 244 of the handle 240. The engagement tabs 244 at this point are disposed in the "long ends" of the oval-shaped opening 270. Upon insertion of the needle element 242 into the cannula 212, the distal region 230 of the coupling element 218 of cannula 212 will enter the space 246 of the handle 240 such that the medial protrusions 248 are aligned with (but not yet engaging) the engagement region 231 of the coupling element 218. At this point, a user would then rotate the lock collar 216 90° to a second position such that the protrusions 272 rest in against the engagement tabs 244 and the engagement tabs 244 rest in the "narrow sides" of the oval-shaped opening 270, as shown in FIG. 45. Due to the oval-shaped nature of the opening 270, upon rotation of the lock collar 216, the engagement tabs 244 will be forced toward one another, and the medial protrusions 248 will come in contact with and positively engage the engagement region 231. As noted previously, this positive engagement prevents the cannula 212 from moving. At the same time, the lock collar 216 serves to lock the engagement tabs 214 in place, effectively locking the cannula 212 and the stylet 214 together.

With reference to FIGS. 46-50, the pedicle access system 210 may be provided with a retractable insulation sheath 217 to electrically insulate the cannula 212 and stylet 214. The insulation sheath 217 may be composed of a non-conductive material or coated with a non-conductive polymer coating to insulate the sheath 217. This prevents shunting of electrical current during pilot hole formation, increasing the efficiency with which the stimulation current is delivered to the target area. Referring to FIG. 46, the insulation sheath 217 includes an insulation tube 274 and a housing member 276. As seen in FIG. 47, the insulation tube comprises a cannulated, elongated and generally cylindrical member having a proximal end 278 and a distal end 280. The proximal end 278 includes at least one tab 282 configured to slideably engage the housing member 276 as set forth below. In the example shown in FIG. 47, the insulation tube 274 includes a pair of tabs 282 positioned opposite one another, however any number of tabs 282 may be provided without departing from the scope of the invention. The distal end 280 may be provided with a generally tapered surface 284 to allow for an improved interface with the bone.

Referring to FIGS. 46 & 48, the housing member 276 comprises an elongated generally cylindrical member having a proximal end 286, a distal end 287 and an interior lumen 288. The proximal end 286 includes a shaped engagement feature 289 (e.g. a recess as shown) dimensioned to engage a sheath attachment element 292 described in further detail below. The housing member 276 further includes at least one elongated track 290 in the form of a cutout section extending substantially the length of the housing member 276. The track 290 is dimensioned to slideably receive the tabs 282 of the insulation tube 274 such that the insulation tube 274 is allowed to migrate within the lumen 288.

Figure 49:
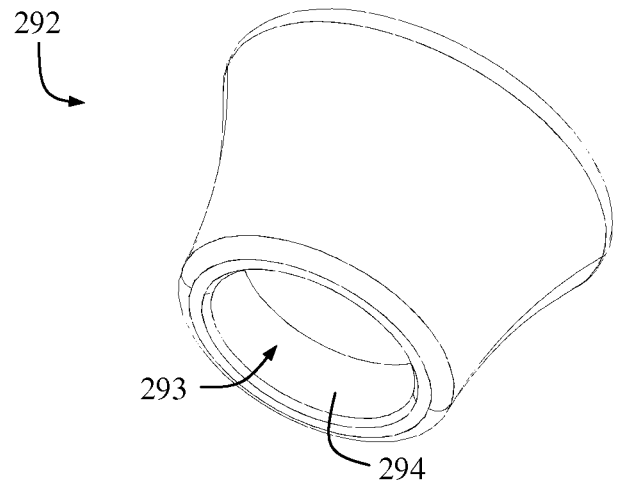
FIGS. 49-50 are perspective views of a sheath attachment element forming part of the pedicle access system of FIG. 31.
Figure 50:
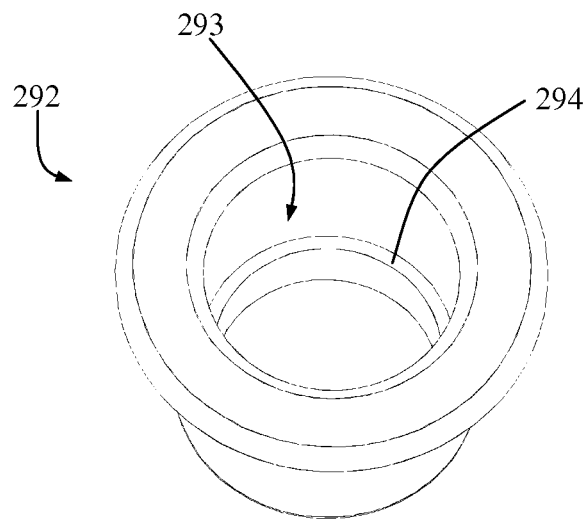
Figure 51:
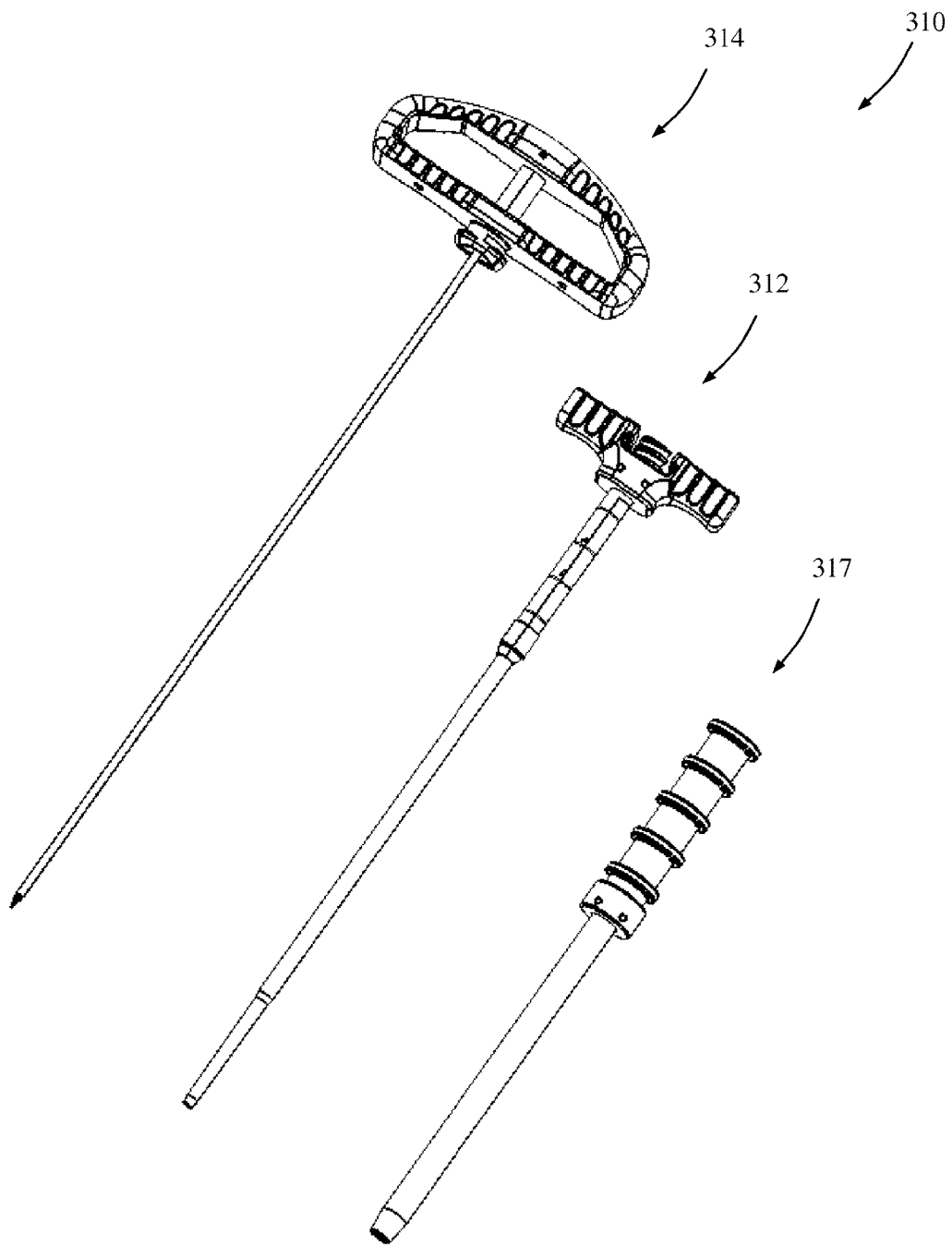
FIG. 51 is an exploded perspective view of a pedicle access system according to another alternative embodiment of the present invention.

With reference to FIGS. 49-50, an example of a sheath attachment element 292 is shown. The sheath attachment element 292 may be provided as a generally cylindrical member having an interior lumen 293. Sheath attachment element 292 is dimensioned to provide a snap-fit engagement with both the housing member 276 and the coupling element 218 of cannula 212. The lumen 293 is provided with a first ridge 294 near a distal end for secure engagement with recess 289 of the housing member 276. Similarly, the lumen 293 is provided with a second ridge (not shown) near a proximal end for engagement with recess 237 of the coupling element 218 (FIG. 37). During assembly of the pedicle access system 210, the retractable insulation sheath 217 may be provided with the sheath attachment element 292 mated to the housing member 276. The cannula 212 is then inserted into the insulation sheath 217 and sheath attachment element 292 will then engage the coupling element 218, thus securely attaching the insulation sheath 217 to the pedicle access system 210.

Figure 32:
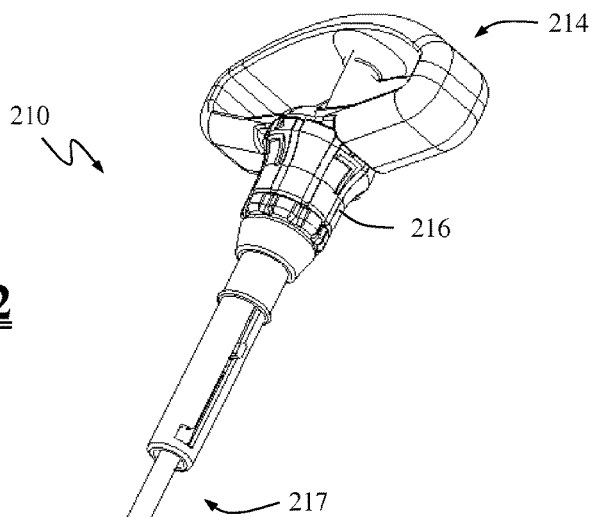
FIGS. 32-33 are perspective views of an assembled pedicle access system of FIG. 31.
Figure 33:
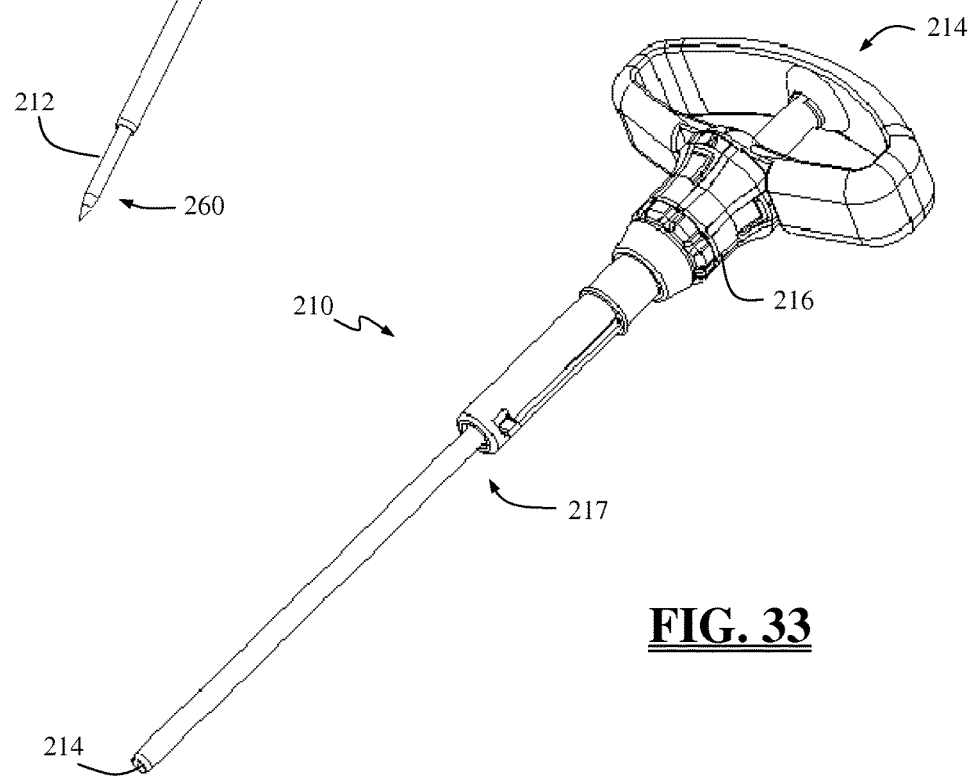
Figure 34:
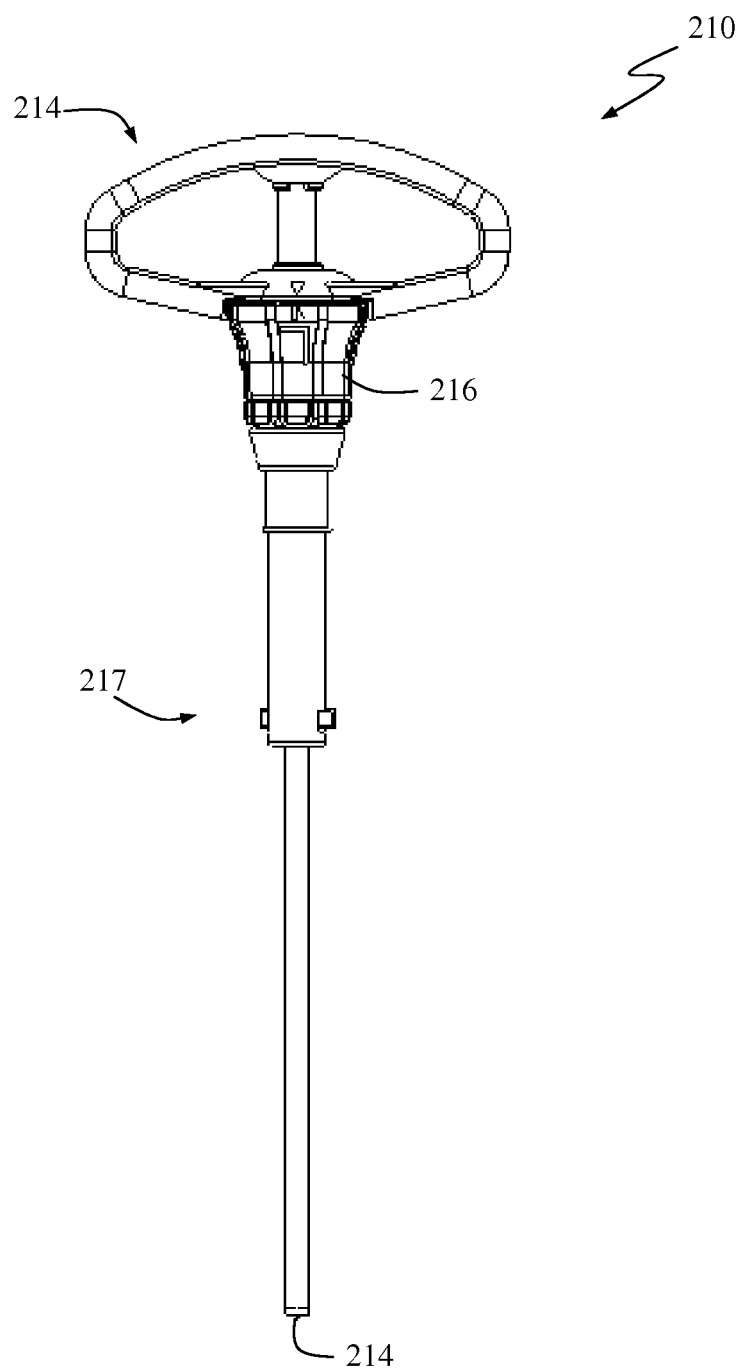
FIG. 34 is a front view of the pedicle access system of FIG. 32.

In use, the pedicle access system 210 is provided with the insulation tube 274 in a first, fully extended position (e.g. FIG. 33). The insulation tube 274 will remain in this position as the pedicle access system 210 is advanced through an operative corridor to a bony target site (e.g. a pedicle). Upon initial engagement with the bony structure, the tip 258 of the needle element 242 and the distal end 280 of the insulation tube 274 may contact the bone at approximately the same time. At this point the user may want to begin monitoring the integrity of the pilot hole formation by using a stimulation signal as described below. As the needle 242 is advanced into the bone, forming a pilot hole, the distal end 280 remains engaged to the outside surface of the bone. At the same time, the proximal end 278 (including tabs 282) of the insulation tube will advance proximally along the track 290 of the housing member 276. Due to the insulated nature of insulation tube 274, the portion of needle element 242 and cannula 212 that protrude from insulation tube 274 effectively constitute a stimulation region 260 (FIG. 32). As the needle 242 and cannula 212 are advanced into the bony structure (and the insulation tube 274 remains on the outside of the bony structure), the stimulation region 260 becomes larger. Upon completion of the pilot hole formation, the needle 242 and cannula 212 are withdrawn from the bony structure, and the pedicle access system 210 may be removed from the operative corridor. A spring (not shown) or other control mechanism may be provided to limit the extent of migration of the insulation tube 274 and/or provide a means for the insulation tube 274 to bias toward returning to the fully extended position upon removal of the needle 242 from the pilot hole in the pedicle.

FIGS. 51-63 illustrate an example of a pedicle access system 310 according to a further alternative embodiment of the present invention. The pedicle access system 310 includes a cannula 312, a stylet 314, and a retractable insulation sheath 317. As shown and described herein, the cannula 312, stylet 314 and retractable insulation sheath 317 are generally cylindrical in shape. However, it should be understood that cannula 312, stylet 314 and sheath 317 may be provided in any suitable shape having any suitable cross-section (e.g. generally oval or polygonal) without deviating from the scope of the present invention. Pedicle access system 310 may be used to percutaneously approach the pedicle, initiate pilot hole formation, and conduct a stimulation signal to the target site for the purposes of performing a pedicle integrity assessment during formation of the pilot hole. To do this, the cannula 312 and stylet 314 may be lockingly mated and inserted through an operating corridor to the pedicle target site, using the handle portion 340 of the stylet 314 to facilitate easy movement and positioning of pedicle access system 310. The pedicle access system 310 may be driven into the bone at the target site to form a pilot hole while a stimulation signal is applied and conducted to the target site to assess the integrity of the pedicle during pilot hole formation. The retractable insulation sheath 317 functions to ensure maximum efficiency and consistency of the stimulation signal when performing pedicle integrity assessments by limiting or preventing shunting of the signal to tissue above the pedicle while also avoiding current density issues that may be encountered when focusing the stimulation signal into the pilot hole through a fixed point.

With specific reference to FIGS. 52-53, the retractable sheath includes a tubular insulation member 374, having a proximal end 378 and a distal end 380, extending from a connecting member 376 described in greater detail below. In an initial position (shown in FIG. 53), the tubular insulation member 374 is fully extended such that it extends at least to the tip 358 of the stylet 314. When forming the pilot hole in a pedicle (or other piece of bone), the stylet 314 will advance into the bone while the insulation sheath remains outside the bone (a position shown by way of example in FIG. 52). Due to the insulative properties of the sheath 317, the electrical current will be directed into the pilot hole by the exposed portion of the cannula 312 and stylet 314 (the size of which increases to match the depth of the pilot hole as the sheath 317 retracts) while prevented from current shunting outside of the hole by the sheath 317.

Figures 56, 57:
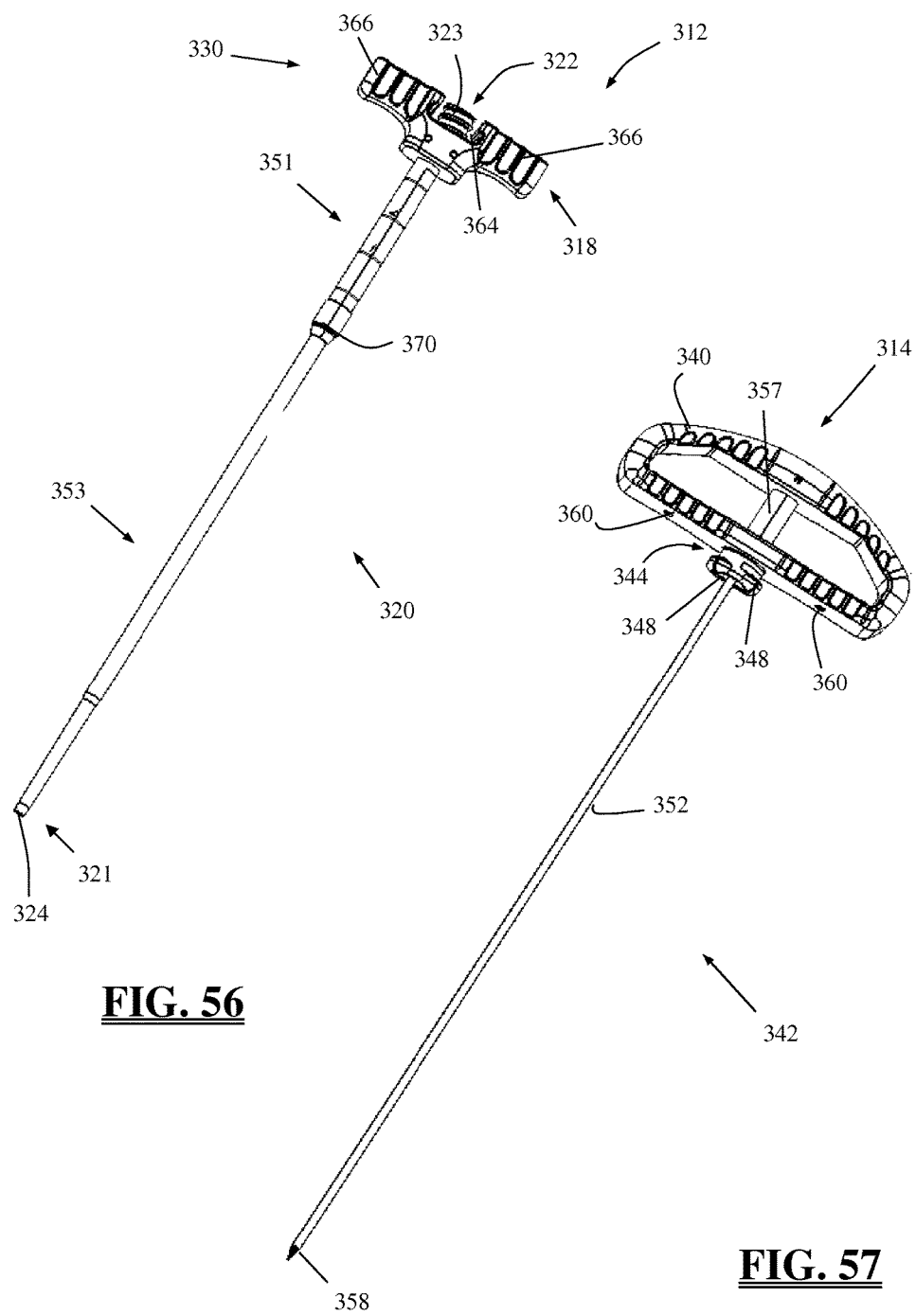
FIG. 56 is a perspective view of a cannula forming part of the pedicle access system of FIG. 51.
FIG. 57 is a perspective view of a stylet forming part of the pedicle access system of FIG. 51.
Figure 62:
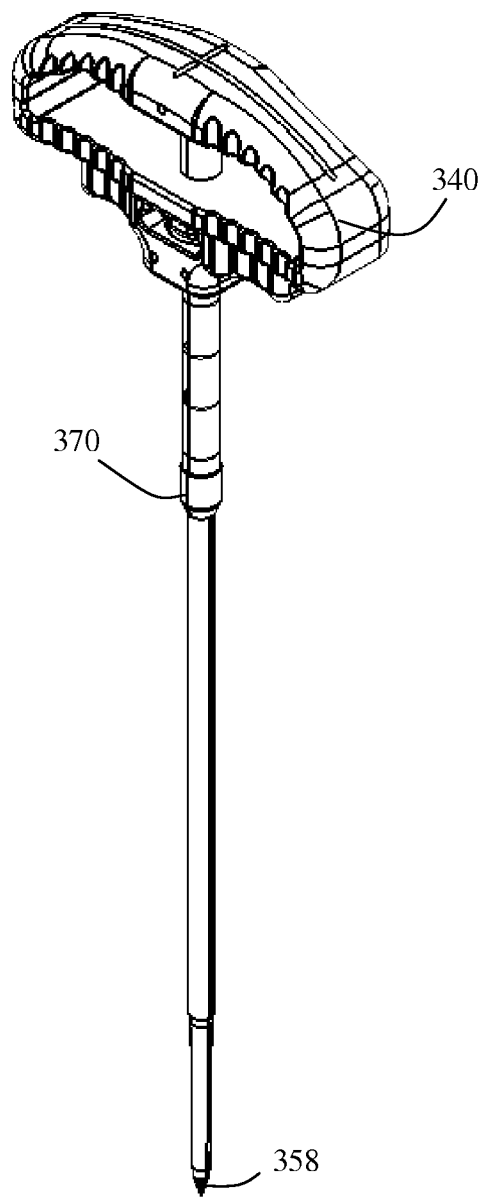
FIG. 62 is a perspective view of the cannula of FIG. 56.
Figure 63:
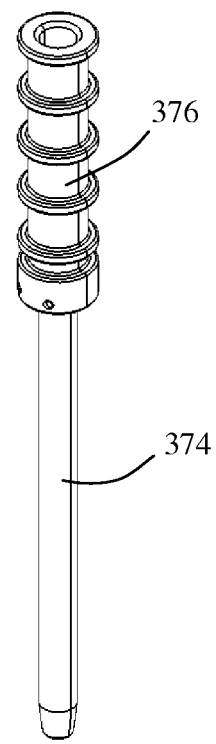
FIG. 63 is a perspective view of a retractable sheath assembly forming part of the pedicle access system of FIG. 51.

FIG. 56 illustrates an example of a cannula 312 forming part of pedicle access system 310 of the present invention. Cannula 312 includes a coupling element 318 and an elongated shaft 320. An interior lumen extends through the cannula 312 from a first opening 322, having a threaded luer lock 323 located at the proximal end 330 of the cannula 312 to a second opening 324 located at the distal end 321 of the elongated shaft 320. The interior lumen is dimensioned to receive the stylet 314 therethrough. The threaded luer lock 323 may be used to connect other apparatus to the cannula 312, for example, a syringe to withdraw or introduce aspirate or a cement delivery vehicle to deliver cement to the bone through the cannula 312.

Elongated shaft 320 has an upper region 351 and a lower region 353. The upper region 351 has a diameter approximating that of the inner diameter of the retractable insulation sheath 317 such that the retractable sheath may slide along the elongated shaft between the initial position and the exposed position. The lower region 353 has a diameter approximating that of the needle element 342 of stylet 314 such that the elongated shaft penetrates into the pedicle with the stylet 314. Elongated shaft 320 may include any number of additional diameter changes incorporated along its length without deviating from the scope of the present invention. The elongated shaft 320 may be composed of any conductive material such as, for example, metal.

FIGS. 57 and 60-61 illustrate an example of a stylet 314 forming part of the pedicle access system 310. Stylet 314 includes a handle portion 340 and a needle element 342. The handle portion 340 may (by way of example) resemble a T-handle for providing a user with a suitable gripping means. By way of example only, the handle portion 340 may have a substantially hollow interior that is not fully enclosed. Locking cylinder 344 extends generally perpendicularly from the handle 340 and includes a pair of radial engagement ridges 348 protruding outward such that the end of the locking cylinder has a larger diameter according to a first direction in line the handle portion 340 and a smaller diameter according to a second direction perpendicular to the handle portion 340. A boss 360 is located on the under surface 359 of the handle on each side of the locking cylinder 344. By way of example only, the boss 360 is circular shaped, though other shapes may also be suitable As described further below, this configuration allows the stylet 314 and the cannula 312 to be lockingly engaged.

The needle element 342 comprises an elongated shaft 352 having a shaped tip 358 and an attachment element 357. The attachment element 357 is situated within the hollow of handle portion 340 and provides a point of contact for an electrical stimulation source (e.g. a clip attached to an electrical source). Elongated shaft 352 extends distally from attachment region 357 (though a lumen in locking cylinder 344, not shown) and generally perpendicularly from the handle 340. Needle element 342 is dimensioned to be inserted through the interior lumen of cannula 312. The shaped tip 358 may have any form or shape capable of being driven into the pedicle to create a pilot hole. By way of example only, shaped tip 358 may have a beveled or double diamond form. When needle element 342 is fully inserted into cannula 312, at least a portion of the shaped tip 358 may protrude slightly from the second opening 324 of cannula 312. Needle element 342 may preferably be composed of any conductive material such as, for example, metal.

With reference to FIG. 58-59, the coupling element 318 of cannula 312 comprises a capture region 364 located in between side extensions 366. The capture region 364 is dimensioned to receive the locking cylinder 344 to securely mate the cannula 312 with the handle 340. The capture region has a lower bore 367 diameter that approximates the larger diameter of the locking cylinder (i.e. the diameter including the engagement ridges) and a bore opening 369 diameter that approximates the smaller diameter of the locking cylinder (i.e. the diameter orthogonal to the engagement ridges). The locking cylinder 344 has an open central cavity 345 to receive the lure lock 323 when the cannula 312 and stylet 14 are engaged. Thus, to engage the stylet 314 with the cannula 312, the handle 340 is aligned perpendicular to the coupling element 318 and the needle element 342 is inserted into the opening 322 though the lure lock 322 until the locking cylinder 344 completely receives the lure lock 323 therein. The handle 340 is then rotated relative to the connecting element 318 until the engagement ridges 348 lockingly engage within lower bore 367 of the capture region 364. The upper surface 365 of each side extension 366 contains a detent 368 that is complementary to the bosses 360 on handle 340 and as the handle 340 is rotated into alignment with the coupling element 318 the detents 368 engage the bossed 360, preventing unwanted unlocking of the handle 340 and coupling element 318.

A friction bearing 370 situated on the upper region 351 is dimensioned to positively engage the inner diameter of the retractable sheath. By way of example, the friction bearing 370 is composed of a polymer material, such as nylon. The diameter of the friction bearing 370 is preferably such that the retractable sheath 374 will not move along the elongated shaft without the application of force to the sheath. In this manner, the surgeon may utilize the sheath 374, and particularly the connector element 376, to handle the pedicle access system 310 without the cannula 312 and/or stylet 314 moving relative to the sheath. According to another contemplated embodiment, the friction bearing may be positioned inside the retractable sheath 317 rather than on the elongated shaft 320. By way of example, the inside of the sheath may be fitted with an O-ring. A ridge may be positioned on the elongated shaft proximal to the O-ring such that the sheath 374 will not travel beyond the initial position (e.g. such that the sheath cannot be removed from the elongated shaft 320 completely). According to another contemplated embodiment, the O-ring may be replaced with a coil spring (positioned on either the elongated shaft 320 or within the retractable sheath 317. Depth markings provided on the upper region 351 indicate the depth to which the elongate shaft 320 is penetrated into the pedicle.

In use, the pedicle access system 310 is provided with the insulation tube 374 in a first, fully extended position (e.g.

Figures 52, 53:
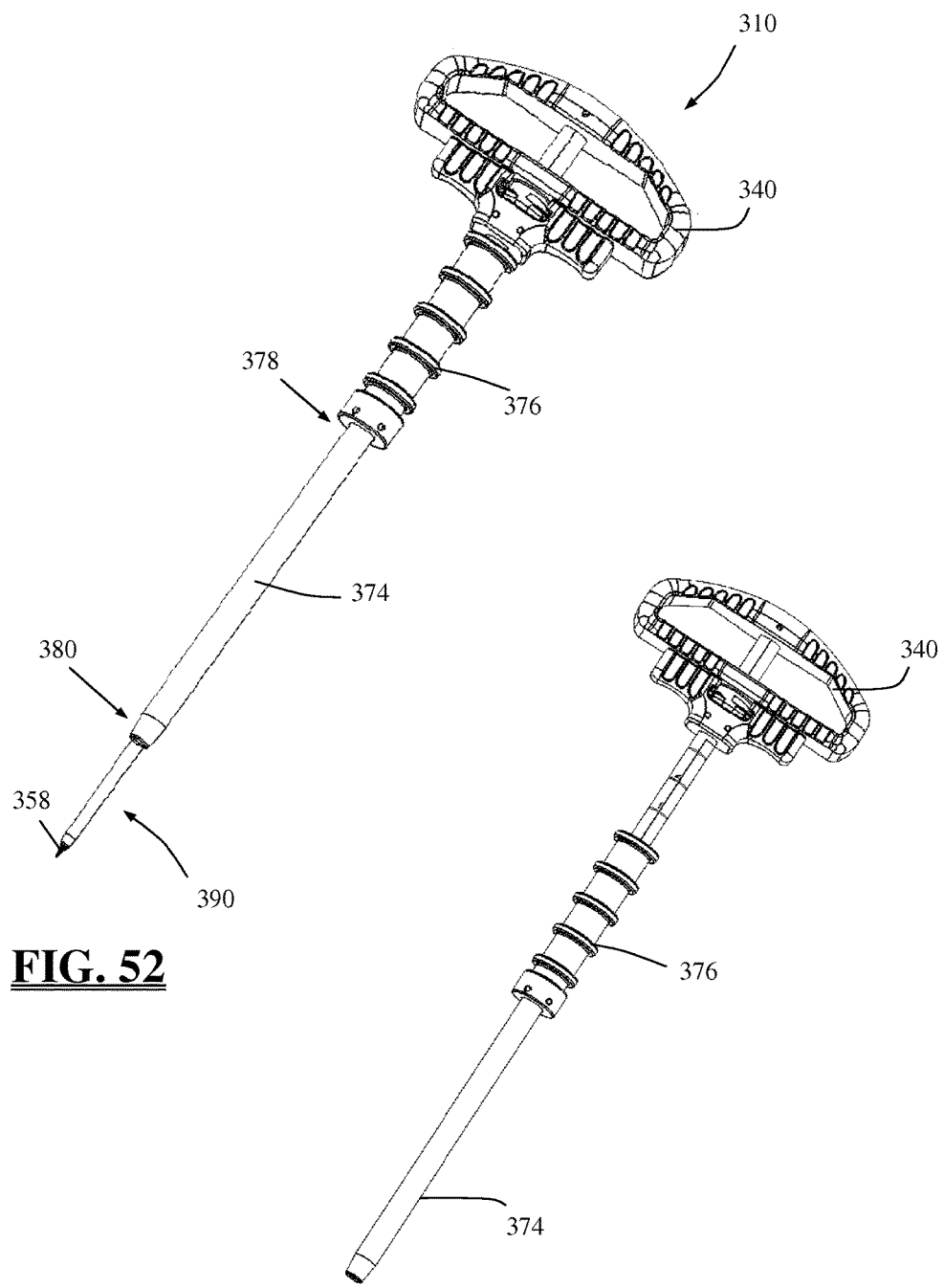
FIG. 52 is a perspective view of the pedicle access system of FIG. 51, showing a retractable sheath in a raised position.
FIG. 53 is a perspective view of the pedicle access system of FIG. 51, showing a retractable sheath in a lowered position.
Figure 54:
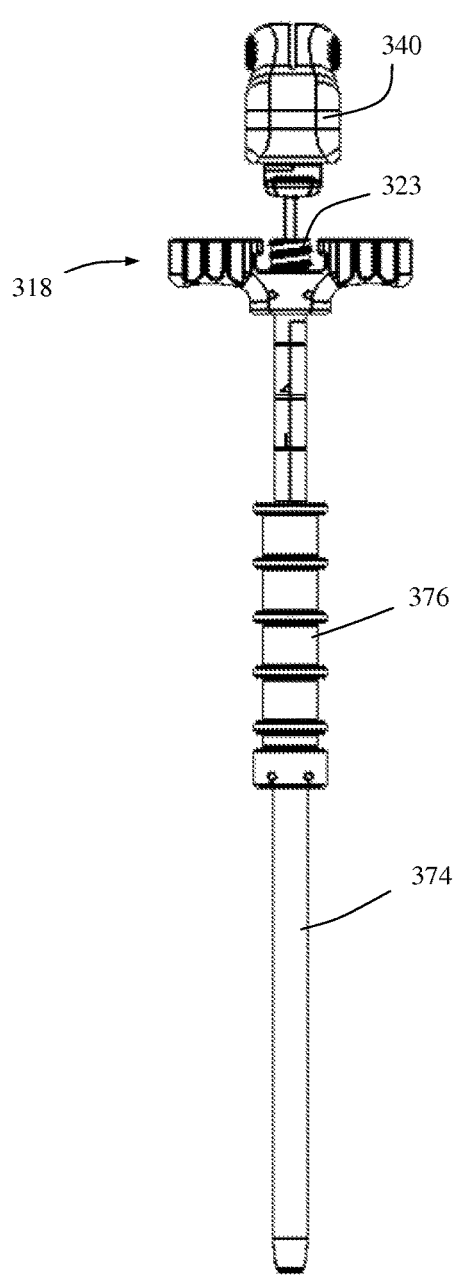
FIGS. 54-55 are front and side views, respectively, of the cannula of the pedicle access system of FIG. 51 with the stylet in a detached position.
Figure 55:
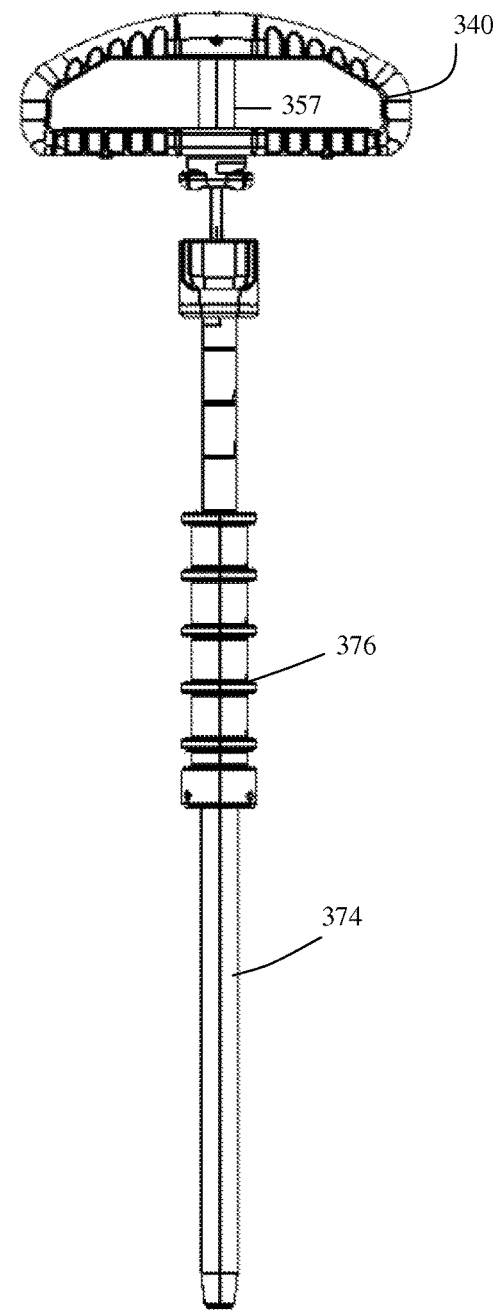

FIG. 52). The insulation tube 374 will remain in this position as the pedicle access system 310 is advanced through an operative corridor to a bony target site (e.g. a pedicle). Upon initial engagement with the bony structure, the tip 358 of the needle element 342 and the distal end 380 of the insulation tube 374 may contact the bone at approximately the same time. At this point the user may want to begin monitoring the integrity of the pilot hole formation by delivering a stimulation signal as described below. As the needle 342 penetrates into bone forming a pilot hole, the distal end 380 engages the outside surface of the bone which prevents further advancement of the insulation tube 374 relative to the bone. Due to the insulated nature of insulation tube 374, the portion of needle element 342 and cannula 312 that protrude from insulation tube 374 effectively constitute a stimulation region 390 (FIG. 52). As the needle 342 and cannula 312 are advanced into the bony structure (and the insulation tube 374 remains on the outside of the bony structure), the stimulation region 390 becomes larger. Upon completion of the pilot hole formation, the needle 342 and cannula 312 are withdrawn from the bony structure, and the pedicle access system 310 may be removed from the operative corridor. A spring (not shown) or other control mechanism may be provided to limit the extent of migration of the insulation tube 374 and/or provide a means for the insulation tube 374 to bias toward returning to the fully extended position upon removal of the needle 342 from the pilot hole in the pedicle.

FIGS. 64-72 illustrate an example of a pedicle access system 410 according to a further alternative embodiment of the present invention. The pedicle access system 410 includes a cannula assembly 412, a retractable sheath 417, and a stylet 414. As shown and described herein, the cannula 412, stylet 414 and retractable insulation sheath 417 are generally cylindrical in shape. However, it should be understood that cannula 412, stylet 414 and sheath 417 may be provided in any suitable shape having any suitable cross-section (e.g. generally oval or polygonal) without deviating from the scope of the present invention.

The pedicle access system 410 may be used to percutaneously approach the pedicle, initiate pilot hole formation, and conduct a stimulation signal to the pilot hole for the purposes of performing a pedicle integrity assessment during formation of the pilot hole. To do this, the cannula assembly 412 and stylet 414 may be lockingly mated (as shown in FIG. 64) and inserted through an operating corridor to the pedicle target site. The retractable sheath 417 is preferably permanently assembled to the cannula assembly 412 (best shown in FIG. 65) and is slidably mated to the cannula assembly 412 in order to allow the retractable sheath 417 to translate relative to the cannula assembly 412. The pedicle access system 410 may be driven into the bone at the target site to form a pilot hole while a stimulation signal is applied to assess the integrity of the pedicle during pilot hole formation. The retractable insulation sheath 417 functions to ensure maximum efficiency and consistency of the stimulation signal when performing pedicle integrity assessments by limiting or preventing shunting of the signal to tissue above the pedicle while also avoiding current density issues that may be encountered when focusing the stimulation signal into the pilot hole through a fixed point.

Figure 66:
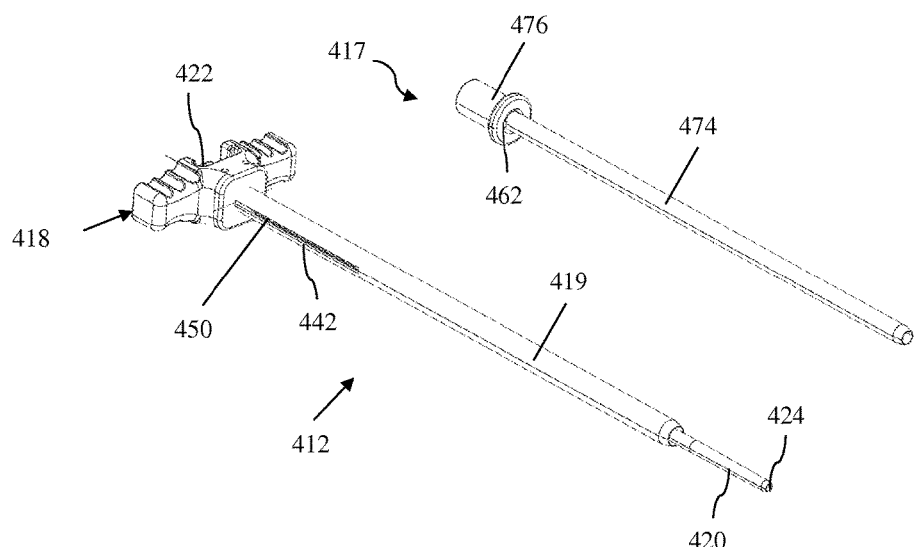
FIG. 66 is a partially exploded view showing the retractable sheath and cannula forming a part of the pedicle access system of FIG. 64.

FIG. 66 illustrates an example of a cannula 412 forming part of pedicle access system 410 of the present invention. Cannula 412 includes a coupling element 418, an outer sheath 419 and an inner cannula 420. An interior lumen extends through the inner cannula 420 from a first opening 422 through a threaded luer lock 423 located at the proximal end of the cannula 412 to a second opening 424 located at the distal end of the inner cannula 420. The interior lumen is dimensioned to receive the stylet 414 therethrough. The proximal ends of the inner cannula 420 and outer sheath 419 are securely mated to the coupling element 418 with the inner cannula 420 concentric to the outer sheath 419. Additionally, the inside diameter of the outer sheath 419 is larger than the outer diameter of the inner cannula 420 and allows sufficient space therebetween for the retractable sheath 417 to longitudinally slide between the outer sheath 419 and inner cannula 420. The fixed outer sheath 419 provides increased handling characteristics to the pedicle access system 410 by providing for a fixed grasping surface along the majority of the length. The outer sheath is preferably insulated while the inner cannula 420 may be composed of any conductive material such as metal.

Figure 67:
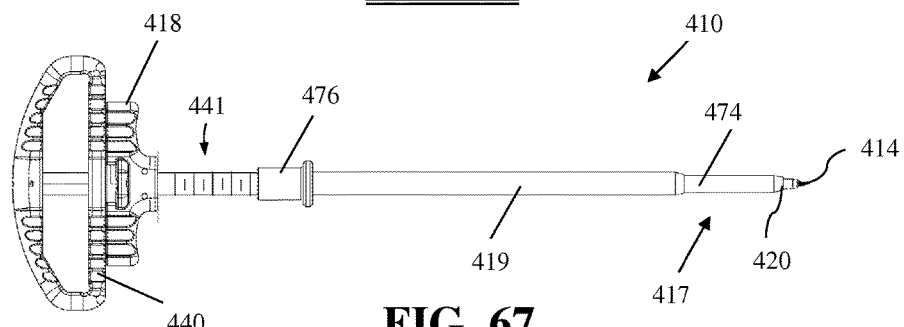
FIG. 67 is a side view of the pedicle access system of FIG. 64, showing a retractable sheath in an extended position.
Figure 68:
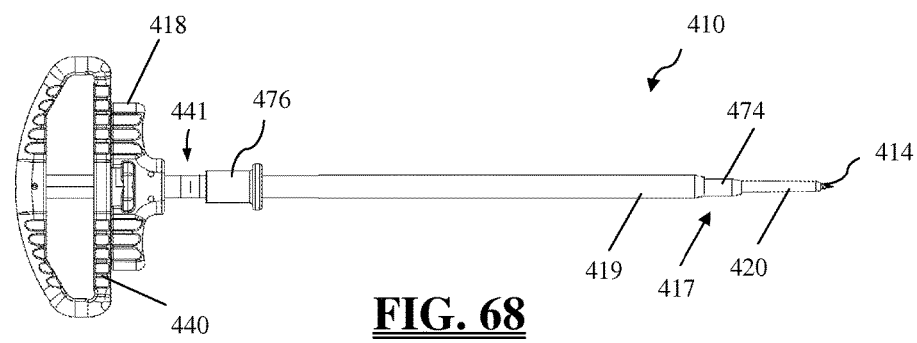
FIG. 68 is a perspective view of the pedicle access system of FIG. 64, showing a retractable sheath in a retracted position.

With specific reference to FIGS. 67-68, the retractable sheath includes a tubular insulation member 474, having a proximal end 478 and a distal end 480, extending from a connecting member 476. In an initial position (shown in FIG. 67), the tubular insulation member 474 is fully extended such that it extends close to or beyond the tip 458 of the stylet 414 and opening 424 of inner cannula 420. When forming the pilot hole in a pedicle (or other piece of bone), the stylet 414 and inner cannula 20 will advance into the bone while the insulation sheath remains outside the bone (a position shown by way of example in FIG. 68). Due to the insulative properties of the retractable sheath 417, the electrical current will be directed into the pilot hole by the exposed portion of the cannula 412 and stylet 414 (the size of which increases to match the depth of the pilot hole as the retractable sheath 417 retracts) and be prevented from from shunting to tissue outside of the hole by the retractable sheath 317.

A spring 450 housed in the cannula interacts with the proximal end of the retractable sheath 417 to bias the retractable sheath 417 towards the fully extended position until the stylet 414 and cannula 412 are driven into a bone. As the stylet 414 and cannula 412 penetrate the bone, the retractable sheath 417 retracts as the distal end 480 engages the bone surface. The tubular insulation member 474 of the sheath 417 longitudinally slides between the outer sheath 419 and inner cannula 420 of the cannula 412. The connecting member 476 of the sheath 417 longitudinally slides along the outer surface of the outer sheath 419 of the cannula 412. Tracks 442 that extend along a portion of the outer sheath 419 provide for a coupling pathway between the connecting member 476 and the tubular insulation member 474. The connecting member 476 and tubular insulation member 474 are securely coupled to each other at coupling junctions 462 which extend through the tracks 442. The tracks 442 also restrict the longitudinal travel of the retractable sheath 417, thus preventing the retractable sheath 417 from translating to far relative to the cannula 412. Depth markings 441 may be provided along the outer sheath 419 such that the position of the connecting member 476 (of the retractable sheath 417) relative to the depth markings indicates the approximate depth the cannula 412 and stylet 414 have penetrated into the pedicle.

FIG. 65 illustrates an example of a stylet 414 forming part of the pedicle access system 410. Stylet 414 includes a handle portion 440 and a needle element 442. The handle portion 440 may (by way of example) resemble a T-handle for providing a user with a suitable gripping means. By way of example only, the handle portion 440 may have a substantially hollow interior that is not fully enclosed. Locking cylinder 444 extends generally perpendicularly from the handle 440 and includes a pair of radial engagement ridges 448 protruding outward such that the end of the locking cylinder has a larger diameter according to a first direction in line the handle portion 440 and a smaller diameter according to a second direction perpendicular to the handle portion 440. A boss 460 is located on the under surface 459 of the handle on each side of the locking cylinder 444. By way of example only, the boss 460 is circular shaped, though other shapes may also be suitable As described further below, this configuration allows the stylet 414 and the cannula 412 to be lockingly engaged.

The needle element 442 comprises an elongated shaft 452 having a shaped tip 458 and an attachment element 457. The attachment element 457 is situated within the hollow of handle portion 440 and provides a point of contact for an electrical stimulation source (e.g. a clip attached to an electrical source). Elongated shaft 452 extends distally from attachment region 457 (though a lumen in locking cylinder 444, not shown) and generally perpendicularly from the handle 440. Needle element 442 is dimensioned to be inserted through the interior lumen of inner cannula 420. The shaped tip 458 may have any form or shape capable of being driven into the pedicle to create a pilot hole. By way of example only, shaped tip 458 may have a beveled or double diamond form. When needle element 442 is fully inserted into the inner cannula 420, at least a portion of the shaped tip 458 may protrude slightly from the second opening 424. Needle element 442 may preferably be composed of any conductive material such as, for example, metal.

With reference to FIGS. 69-72, the coupling element 418 of cannula 412 comprises a capture region 464 located in between side extensions 466. The capture region 464 is dimensioned to receive the locking cylinder 444 to securely mate the cannula 412 with the handle 440. The capture region has a lower bore 467 diameter that approximates the larger diameter of the locking cylinder (i.e. the diameter including the engagement ridges) and a bore opening 469 diameter that approximates the smaller diameter of the locking cylinder (i.e. the diameter orthogonal to the engagement ridges). The locking cylinder 444 has an open central cavity 445 to receive the lure lock 423 when the cannula 412 and stylet 414 are engaged. Thus, to engage the stylet 414 with the cannula 412, the handle 440 is aligned perpendicular to the coupling element 418 and the needle element 442 is inserted into the opening 422 though the lure lock 422 until the locking cylinder 444 completely receives the lure lock 423 therein. The handle 440 is then rotated relative to the connecting element 418 until the engagement ridges 448 lockingly engage within lower bore 467 of the capture region 464. The upper surface 465 of each side extension 466 contains a detent (not shown) that is complementary to the bosses 460 on handle 440 and as the handle 440 is rotated into alignment with the coupling element 418 the detents 468 engage the bosses 460, preventing unwanted unlocking of the handle 440 and coupling element 418.

Figure 73:
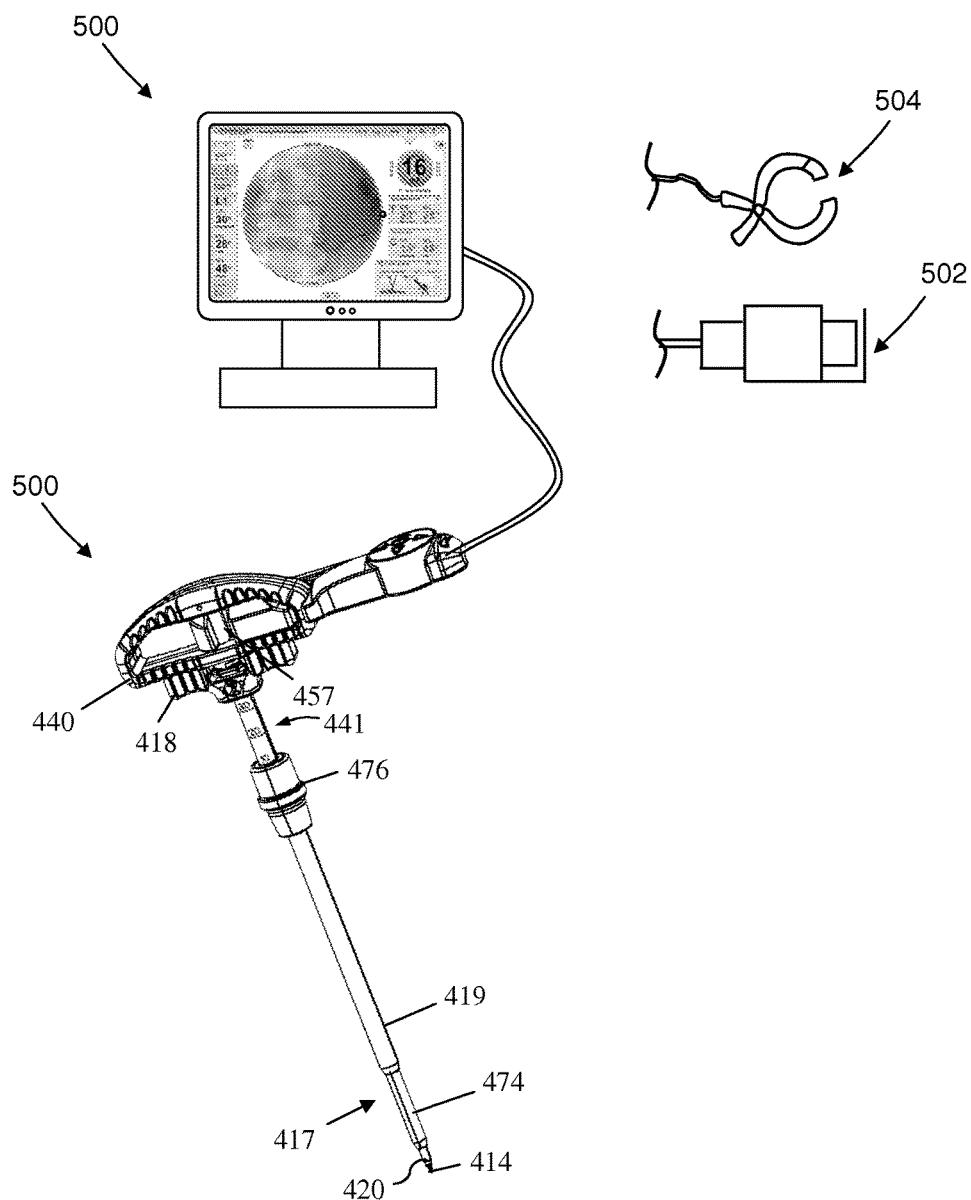
FIG. 73 is a perspective view of an example of a neurophysiology system capable of connecting to the pedicle access systems of FIGS. 1, 19, 31, 51 and 64 to conduct neurophysiological monitoring.

The pedicle access systems 10, 110, 210, 310 and 410 described above may be used in combination with neurophysiology monitoring systems and methods to conduct pedicle integrity assessments while cannulating the pedicles. By way of example only, the pedicle access systems 10, 110, 210, 310 and 410 may be used in combination with the system and methods shown and described in Int'l Patent App. Ser. Nos. PCT/US02/22247, filed on Jul. 11, 2002, Int'l Patent App. Ser. No. PCT/US02/22247, PCT/2008/124079, filed on Apr. 3, 2008, PCT/US2008/012121, filed on Oct. 28, 2008 the contents of which are each hereby incorporated by reference into this disclosure as set forth herein in their entireties. With reference to FIG. 73, one such neurophysiology system 500 for performing pedicle integrity assessments is depicted, including an electric coupling device 502 capable of coupling to the embodiments 210, 310 and 410 (e.g. the embodiments with handle cutouts) to the pedicle access systems described above the system 500. Alternate style connectors, including a plunger style connector 502 and a clamp style connector 504 are also shown and are capable of coupling all of the embodiments 10, 110, 210, 310 and 410 to the pedicle access systems described above the system 500.

The neurophysiology system 500 performs pedicle integrity assessments by determining the amount of electrical communication between a stimulation signal and the nerve root lying outside the pedicle. To do this, a stimulation signal is applied to the pilot hole through one of the access needles as described above. Electrodes positioned over the appropriate muscles measure the EMG responses corresponding to the delivered stimulation signals. The relationship between the EMG response and the stimulation signal is then analyzed by the system and the results are conveyed to the user on the system display. The basic theory underlying the pedicle integrity test is that given the insulating character of bone, a higher stimulation current (or current density) is required to evoke an EMG response when the stimulation signal is applied to an intact pedicle as opposed to a breached pedicle. Thus, if EMG responses are evoked by stimulation currents (or current densities) lower than a predetermined safe level, the surgeon may be alerted that there is a possible breach. The neurophysiology system may be provided with software capable of compensating for multiple safe stimulation thresholds based on different current densities being applied to the pedicle by certain geometries of different instruments.

In another significant aspect of the present invention, the pedicle access system 10 may be used in conjunction with spinal fixation systems that require access to pedicle target sites and need pilot holes, including but not limited to those systems shown and described in commonly owned and co-pending U.S. patent application Ser. No. 11/031,506 filed Jan. 6, 2005, and commonly owned and co-pending Int'l Patent App. Ser. No. PCT/US05/032300 filed Sep. 8, 2005. After positioning the pedicle access system 10 on the desired pedicle target site and safely forming a pilot hole as described above, the T-handle 16 and stylet 14 may be unlocked and removed from the cannula 12, leaving the cannula 12 positioned in the pilot hole. Guide wires subsequently used by the spinal fixation systems may then be safely deployed to the pilot hole through the cannula 12. Once the guide wire is in position the cannula 12 may be removed from the target site and the surgeon may commence use of the surgical fixation system.

While the invention is susceptible to various modification and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the scope and spirit of the invention as defined herein.

What is claimed is:

1. A needle assembly system for use in a medical procedure, comprising:
   a cannula assembly including concentric inner and outer cannulas wherein the inner cannula has a distal end and a first length and the outer cannula has a distal end and a second length shorter than the first length, an insulated sheath situated between the inner cannula and the outer cannula, and a spring situated proximal to the insulated sheath and between the inner cannula and outer cannula, said insulated sheath spring biased to a first position in which a distal end of the insulated sheath is proximate the distal end of the inner cannula and movable between a position in which a distal end of the insulated sheath is proximate the distal end of the inner cannula and closer to the distal end of the inner cannula than to the distal end of the outer cannula, and a position in which a distal end of the insulated sheath is proximate the distal end of the outer cannula and closer to the distal end of the outer cannula than to the distal end of the inner cannula; and a stylet disposed through the inner cannula and having a shaped tip that protrudes from the distal end of the inner cannula.

2. The system of claim 1, wherein the outer cannula is also insulated.

3. The system of claim 1, wherein a connector situated outside the outer cannula is attached to the insulated sheath.

4. The system of claim 3, wherein the connector attaches to the insulated sheath through at least one elongated slot proximate a distal end of the outer cannula.

5. The system of claim 3, wherein the outer cannula includes graduated depth markers and the position of the connector relative to the depth marker provides an indication of penetration depth of the shaped tip of the stylet into tissue.

6. The system of claim 1, further including a handle comprising an upper portion and a lower portion separable from the upper portion.

7. The system of claim 6, wherein the upper portion is connected to the stylet and the lower portion is connected to the cannula assembly and the upper and lower portions are lockable to one another to lock the cannula assembly and the stylet together.

8. The system of claim 7, further including a contact that receives electrical stimulation signals from a stimulator via a stimulation clip associated with the stimulator.

9. The system of claim 8, wherein said contact is a conductive surface situated within the upper handle portion attached to the stylet.

10. The system of claim 9, wherein the upper portion of the handle includes a cutout region that securely engages the stimulation clip.

11. The system of claim 1, wherein the stylet is removable from the cannula assembly.

12. The system of claim 11, further including a k-wire advanceable through the inner cannula after the stylet has been removed.

13. The system of claim 1, wherein the shaped tip and the distal end of the inner cannula are adapted to form a hole in bone and a distal end of the insulated sheath is adapted to engage a surface of the bone when the shaped tip and the distal end of the inner cannula are advanced into bone such that the insulated sheath slides relative to the inner cannula and outer cannula as the shaped tip and distal end of the inner cannula are advanced deeper into the bone exposing the exterior of inner cannula to the interior of the bone.

14. A needle assembly system for use in a medical procedure, comprising:

a cannula assembly including concentric inner and outer cannulas wherein the inner cannula has a distal end and a first length and the outer cannula has a distal end and a second length shorter than the first length, and an insulated sheath situated between the inner cannula and the outer cannula and movable between a position in which a distal end of the insulated sheath is proximate the distal end of the inner cannula and closer to the distal end of the inner cannula than to the distal end of the outer cannula, and a position in which a distal end of the insulated sheath is proximate the distal end of the outer cannula and closer to the distal end of the outer cannula than to the distal end of the inner cannula, wherein the insulated sheath is spring biased towards the position proximate the distal end of the inner cannula by a spring positioned between the inner and outer cannulae, a stylet disposed through the inner cannula and having a shaped tip that protrudes from the distal end of the inner cannula, and a connector situated outside the outer cannula and concentric with the outer cannula and attached to the insulated sheath through at least one elongated slot wherein the connector is moveable axially along the outer surface of the outer cannula.

15. The system of claim 14, wherein the outer cannula is also insulated.

16. The system of claim 14, wherein the outer cannula includes graduated depth markers and the position of the connector relative to the depth marker provides an indication of penetration depth of the shaped tip of the stylet into tissue.

17. The system of claim 14, further including a handle comprising an upper portion connected to the stylet, a lower portion connected to the cannula assembly, wherein the lower portion is separable from the upper portion and the upper and lower portions are lockable to one another to lock the cannula assembly and the stylet together.

18. The system of claim 14, further including a contact that receives electrical stimulation signals from a stimulator via a stimulation clip associated with the stimulator.

19. The system of claim 18, wherein said contact is a conductive surface situated within the upper handle portion attached to the stylet.

20. The system of claim 18, wherein the upper portion of the handle includes a cutout region that securely engages the stimulation clip.

21. A needle assembly system for use in a medical procedure, comprising:

a cannula assembly including concentric inner and outer cannulas wherein the inner cannula has a distal end and a first length and the outer cannula has a distal end and a second length shorter than the first length, and an insulated sheath situated between the inner cannula and the outer cannula and movable between a position in which a distal end of the insulated sheath is proximate the distal end of the inner cannula and closer to the distal end of the inner cannula than to the distal end of the outer cannula, and a position in which a distal end of the insulated sheath is proximate the distal end of the outer cannula and closer to the distal end of the outer cannula than to the distal end of the inner cannula, wherein the insulated sheath is spring biased towards the position proximate the distal end of the inner cannula by a spring positioned between the inner and outer cannulae;

a stylet disposed through the inner cannula and having a shaped tip that protrudes from the distal end of the inner cannula; and a handle comprising an upper portion and a lower portion, which is separable from the upper portion, wherein the upper portion is connected to the stylet and the lower portion is connected to the cannula assembly, said upper and lower portion lockable to one another to lock the cannula assembly and stylet together, said handle further including a contact that is configured to receive electrical stimulation signals from a stimulator.

22. The system of claim 21, wherein said contact is a conductive surface situated within the upper handle portion attached to the stylet.

23. The system of claim 22, wherein the upper portion of the handle includes a cutout region that securely engages the stimulation clip.

* * * * *